United States Patent
Chen et al.

(10) Patent No.: US 12,306,082 B2
(45) Date of Patent: May 20, 2025

(54) APPARATUS AND METHOD FOR MONITORING AND RECORDING DISINTEGRATION TIMES FOR PHARMACEUTICAL PRODUCTS

(71) Applicant: Merck Sharp & Dohme LLC, Rahway, NJ (US)

(72) Inventors: Grace Chen, Lansdale, PA (US); Joanna C. Everitt, Upper Black Eddy, PA (US); Sydney Floryanzia, Apex, NC (US); Janakiraman Gopinath, Morris Plains, NJ (US); Prashant I. Shah, Morganville, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 686 days.

(21) Appl. No.: 17/762,253

(22) PCT Filed: Sep. 29, 2020

(86) PCT No.: PCT/US2020/053177
§ 371 (c)(1),
(2) Date: Mar. 21, 2022

(87) PCT Pub. No.: WO2021/067207
PCT Pub. Date: Apr. 8, 2021

(65) Prior Publication Data
US 2022/0334040 A1    Oct. 20, 2022

Related U.S. Application Data

(60) Provisional application No. 62/909,351, filed on Oct. 2, 2019.

(51) Int. Cl.
*G01N 13/00* (2006.01)
*G01N 33/15* (2006.01)
*G01N 35/00* (2006.01)

(52) U.S. Cl.
CPC ............. *G01N 13/00* (2013.01); *G01N 33/15* (2013.01); *G01N 35/00* (2013.01); *G01N 2013/006* (2013.01); *G01N 2035/00198* (2013.01)

(58) Field of Classification Search
CPC ........ G01N 13/00; G01N 33/15; G01N 35/00; G01N 2013/006; G01N 2035/00198
(Continued)

(56) References Cited

U.S. PATENT DOCUMENTS

| | | | |
|---|---|---|---|
| 4,855,821 A | 8/1989 | Swon et al. | |
| 7,021,163 B2 * | 4/2006 | Kyne | G01N 33/15 |
| | | | 73/866 |

(Continued)

FOREIGN PATENT DOCUMENTS

| | | | |
|---|---|---|---|
| CN | 106970202 A | | 7/2017 |
| CN | 113984764 A | * | 1/2022 |

OTHER PUBLICATIONS

Morita et al. "Evaluation of the Disintegration Time of Rapidly Disintegrating Tablets via a Novel Method Utilizing a CCD Camera" Chem. Pharm. Bull. 50(9) pp. 1181-1186 (Year: 2002).*

(Continued)

*Primary Examiner* — John Fitzgerald
(74) *Attorney, Agent, or Firm* — Sylvia A. Ayler; Catherine Fitch

(57) ABSTRACT

Embodiments of the present invention provide an apparatus and method for determining whether a dosage unit of a pharmaceutical drug disintegrates in an immersion fluid of a disintegration tester within a prescribed time limit and to record and transmit to human-accessible output devices the times required. In one implementation, the apparatus comprises a computer system, a motion sensor, a capture device, a fastener for attaching the capture device and motion sensor (Continued)

to the reciprocating arm of the disintegration tester, and one or more data communications interfaces to carry commands and data between the computer system, the motion sensor and the capture device.

20 Claims, 14 Drawing Sheets

(58) Field of Classification Search
USPC .............................................. 73/866, 866.2
See application file for complete search history.

(56) References Cited

U.S. PATENT DOCUMENTS

| 9,534,997 | B2* | 1/2017 | Heng | ................. G01N 13/00 |
| 10,088,464 | B2* | 10/2018 | Blackley | ............ G01N 33/0004 |
| 2005/0003550 | A1 | 1/2005 | Kyne | |
| 2006/0144171 | A1 | 7/2006 | Carlson et al. | |
| 2008/0165354 | A1 | 7/2008 | Rantanen et al. | |
| 2014/0305225 | A1 | 10/2014 | Heng et al. | |
| 2016/0290981 | A1* | 10/2016 | Brinker | ................. G01N 33/15 |
| 2017/0254791 | A1 | 9/2017 | Nink et al. | |

OTHER PUBLICATIONS

Chi, Zhongmei et al., Automatic Dissolution Testing with High-Temporal Resolution for Both Immediate-Release and Fixed-Combination Drug Tablets, Nature, 2019, 1-11, 9:17114.

Markl, Daniel et al., A Review of Disintegration Mechanisms and Measurement Techniques, Pharmaceutical Research, 2017, 890-917, 34.

Rajkumar, Arthi D. et al., Investigating the effect of processing parameters on pharmaceutical tablet disintegration using a real-time particle imaging approach, European Journal of Pharmaceutics and Biopharmaceutics, 2016, 88-96, 106.

* cited by examiner

Region A

| Position | (X,Y) | R | G | B | H | S | V | Depth | Units |
|---|---|---|---|---|---|---|---|---|---|
| 1 | 0,0 | 0 | 0 | 0 | 0 | 0 | 0 | 401 | mm |
| 2 | 1,0 | 0 | 0 | 0 | 0 | 0 | 0 | 401 | mm |
| 3 | 2,0 | 0 | 0 | 0 | 0 | 0 | 0 | 401 | mm |
| 4 | 3,0 | 0 | 0 | 0 | 0 | 0 | 0 | 401 | mm |
| 5 | 4,0 | 0 | 0 | 0 | 0 | 0 | 0 | 401 | mm |

Region B

| Position | (X,Y) | R | G | B | H | S | V | Depth | Units |
|---|---|---|---|---|---|---|---|---|---|
| 1279 | 1278,0 | 0 | 0 | 0 | 0 | 0 | 0 | 401 | mm |
| 1280 | 1279,0 | 0 | 0 | 0 | 0 | 0 | 0 | 401 | mm |
| 1281 | 0,1 | 0 | 0 | 0 | 0 | 0 | 0 | 401 | mm |
| 1282 | 1,1 | 0 | 0 | 0 | 0 | 0 | 0 | 401 | mm |
| 1283 | 2,1 | 0 | 0 | 0 | 0 | 0 | 0 | 401 | mm |
| 1284 | 3,1 | 0 | 0 | 0 | 0 | 0 | 0 | 399 | mm |

Region C

| Position | (X,Y) | R | G | B | H | S | V | Depth | Units |
|---|---|---|---|---|---|---|---|---|---|
| 818,560 | 639,639 | 208 | 208 | 208 | 0 | 0 | .82 | 393 | mm |
| 818,561 | 640,639 | 209 | 209 | 209 | 0 | 0 | .82 | 392 | mm |
| 818,562 | 641,639 | 210 | 210 | 210 | 0 | 0 | .82 | 391 | mm |
| 818,563 | 642,639 | 211 | 211 | 211 | 0 | 0 | .83 | 390 | mm |
| 818,564 | 643,639 | 212 | 212 | 212 | 0 | 0 | .83 | 390 | mm |
| 818,565 | 644,639 | 212 | 212 | 212 | 0 | 0 | .83 | 389 | mm |

Region D

| Position | (X,Y) | R | G | B | H | S | V | Depth | Units |
|---|---|---|---|---|---|---|---|---|---|
| 1,638,398 | 1277,1279 | 0 | 0 | 0 | 0 | 0 | 0 | 401 | mm |
| 1,638,399 | 1278,1279 | 0 | 0 | 0 | 0 | 0 | 0 | 401 | mm |
| 1,638,400 | 1279,1279 | 0 | 0 | 0 | 0 | 0 | 0 | 401 | mm |

FIG.6

(PROPHETIC EXAMPLE)

(PROPHETIC EXAMPLE)

APPARATUS AND METHOD FOR MONITORING AND RECORDING DISINTEGRATION TIMES FOR PHARMACEUTICAL PRODUCTS

CROSS REFERENCE TO RELATED APPLICATIONS

This application is a U.S. National Phase application under 35 U.S.C. § 371 of PCT Application No. PCT/US2020/053177 filed Sep. 29, 2020, which claims priority from U.S. Ser. No. 62/909,351 filed Oct. 2, 2019.

FIELD OF THE INVENTION

The present invention relates to systems, methods and apparatus for monitoring and recording disintegration times for a pharmaceutical drug placed in an immersion fluid of a disintegration testing machine.

BACKGROUND OF THE INVENTION

During the research, development, testing and regulatory compliance stages of bringing pharmaceutical drug products to market, it is frequently necessary or desirable to test whether a dosage unit (such as a tablet, capsule or granule) of the pharmaceutical drug disintegrates within a prescribed time limit when the dosage unit is placed in an immersion fluid under experimental conditions. The experimental conditions are achieved by using a machine called a disintegration tester, comprising a basket-rack assembly, a vessel to hold the immersion fluid, such as a beaker or other container, and a mechanically-operated reciprocating arm. The reciprocating arm repetitively moves the basket-rack assembly and the dosage unit up and down in the immersion fluid in accordance with a prescribed range and frequency of motion.

The conventional way of testing and recording disintegration times for solid pharmaceutical products is to place one or more dosage units of the pharmaceutical product in the basket-rack assembly, lower the basket-rack assembly into the immersion fluid, and have one or more human operators watch the dosage unit disintegrate as the reciprocating arm drives the basket-rack assembly and the dosage unit up and down in the immersion fluid, and then manually record the time required for the dosage unit to disintegrate. Thus, the human operators must decide by visual observation alone when the dosage unit has completely disintegrated.

Consistent with this approach, there are several official regulatory standards for disintegration testing that rely on visual confirmation by human operators to mark the end point of the disintegration process. For example, according to Section <701> of the United States Pharmacopeia (hereinafter "USP <701>"), which covers disintegration procedures and criteria for pharmaceutical tablets and capsules, one of the official procedures and criteria for testing uncoated or plain-coated tablets requires, in general, that a human operator perform the steps of: (1) placing one tablet in each of six tubes of the basket-rack assembly, (2) submerging the basket-racket assembly (containing six tablets in total) in an immersion fluid maintained at a temperature between 35 and 39 degrees Celsius, and (3) switching on the disintegration tester so that the reciprocating arm of the disintegration tester repetitively raises and lowers the basket-rack assembly in the immersion fluid, the reciprocating arm moving at a constant frequency between 20 and 32 cycles per minute through a distance of not less than 53 mm and not more than 57 mm. At the end of a prescribed time limit for the tablet, the human operator must then (4) lift the basket-rack assembly from the fluid, and (5) determine by visual observation whether (or not) all six tablets have disintegrated completely. If all six of the tablets have disintegrated completely, then the disintegration testing requirements are met and no more tablets need to be tested. On the other hand, if one or two of the six tablets tested fail to disintegrate completely, then the human operator must repeat the test on twelve additional tablets, bringing the total number of tablets tested to eighteen tablets. The USP <701> disintegration requirements for uncoated or plain-coated tablets are met if not fewer than sixteen of a total of eighteen tablets tested are disintegrated at the end of the prescribed time limit.

In some situations, it may be necessary or desirable to determine, not whether the dosage unit disintegrates with a prescribe time limit, but exactly how long a dosage unit takes to disintegrate in the immersion fluid of a disintegration tester. In these cases, the human operator typically needs to observe the entire disintegration process, from start to finish, and decide solely through visual observation, when the dosage unit is disintegrated. For some types of tablets or pills, it can take anywhere from ten seconds to four hours for a dosage unit to completely disintegrate. For other types of tablets or pills, it may take longer than four hours for the tablet or pill to completely disintegrate.

The conventional approach of using human operators to confirm complete disintegration by visual inspection, and manually record whether and/or when the dosage units have fully disintegrated, is extremely time consuming, expensive in terms of man hours, and prone to human error. Human operators can, and often do, become distracted while waiting for a drug to disintegrate, and there are often significant differences between different humans, in terms of their physical abilities to discern the exact endpoints of disintegrations in immersion fluids, especially when the immersion fluid becomes cloudy or opaque due to the dosage units dispersing residue and/or insoluble fragments during the disintegration. Moreover, the results are extremely subjective, because those results are based on human observation and interpretation. As a result, the manual approach of using visual confirmation has been highlighted as a significant risk for data integrity problems, frequently necessitating visual confirmation by at least two human operators that the dosage unit has completely disintegrated.

To help mitigate some of these problems, automated techniques for disintegration testing have been introduced, which involve placing on top of each dosage unit a specialized plastic disk with electronic contacts, and programming the disintegration testers to generate an alert or completion signal when the electronic contacts on the bottom of the plastic disks come into contact with a metal mesh located at the bottom of the tube holding the dosage unit. However, the plastic disks with contact probes are not an ideal solution because the weight of the disks on top of the dosage units can interfere with disintegration, and thereby alter disintegration rates. The plastic disks also require regulatory review and validation before they can be used and relied upon for disintegration testing.

Accordingly, there is considerable need in the pharmaceutical industry for a fully automated, consistent and dependable apparatus and method for measuring and recording disintegration times of drug dosage units in disintegration testers, which does not rely on human observation, visual acuity or attention spans, and does not rely on using government regulation-compliant plastic disks with contact probes that can interfere with disintegration, and thereby undermine the integrity of the data.

SUMMARY OF THE INVENTION

Embodiments of the present invention provide an apparatus and method for determining whether a dosage unit of a pharmaceutical drug disintegrates in an immersion fluid of a disintegration tester within a prescribed time limit. In addition, embodiments of the present invention can also be used to determine, record and transmit to human-accessible output devices the times required for dosage units of a drug to disintegrate in the immersion fluid of the disintegration tester. In one implementation, the apparatus comprises a computer system, a motion sensor, a capture device, a fastener for attaching the capture device and motion sensor to the reciprocating arm of the disintegration tester, and one or more data communications interfaces to carry commands and data between the computer system, the motion sensor and the capture device. Beneficially, the apparatus is configured to be used with a conventional disintegration tester, which typically includes a reciprocating arm that repetitively moves the dosage unit up and down in the immersion fluid in accordance with a prescribed range and frequency of motion.

The computer system, which may comprise, for example, a personal computer, a tablet computer, a laptop or notebook computer, a smart cellphone or personal digital assistant, suitably includes a microprocessor, an output device, a system clock, a primary memory, and a secondary memory. The computer system is communicatively connected to the motion sensor, as well as the capture device, by a data communications interface, which may include, without limitation, a universal serial bus (USB) adapter, a wireless radio frequency data communications adapter, an Ethernet adapter, a video graphics adapter, or a combination of two or more such wired or wireless data communications interfaces customarily used in the computer networking and communications industries.

The capture device may comprise, for example, an optical digital camera that generates and transmits to the computer system a stream of successively captured frames (i.e., snapshots), wherein each frame may comprise RGB (red, green, blue) color data or HSV (hue, saturation and value) color data for the dosage unit and the background, or a light detection and ranging (LIDAR) device that produces and transmits to the computer system a stream of successively captured frames, each frame comprising current depth (i.e., distance) data for the dosage unit and the background, or a thermal capture device that generates and transmits to the computer system a stream of successively captured frames, each frame comprising current temperature data for the dosage unit and the background. In some embodiments, the apparatus may include and utilize a combination of two or more capture devices that are all the same type (e.g., all optical digital cameras, all LIDARs, or all thermal capture devices) operating simultaneously to capture separate streams of images of the same disintegrating dosage unit. In other embodiments, the apparatus may utilize a combination of two or more capture devices of different types all operating simultaneously to capture separate streams of images of the same disintegrating dosage unit. When two or more capture devices are utilized, embodiments of the present invention may be configured to generate and record separate disintegration times for each capture device, compare the multiple disintegration times to each other, and select for display or further processing the disintegration time that is the longest. Depending on the circumstances of the testing, embodiments may also be configured to calculate and use the shortest, average or median values of all the separate disintegration times generated by two or more capture devices.

The primary memory includes an application program, or a combination of application programs (i.e., computer software programs, executable code, etc.), having programming instructions that, when executed on the microprocessor, will cause the microprocessor to operate, in conjunction with the primary and secondary memories and the data communications interfaces, to: (i) receive motion data from the motion sensor over the data communications interface, (ii) determine, based on the motion data, that the reciprocating arm is moving in accordance with the prescribed range and frequency of motion, and (iii) after determining that the reciprocating arm is moving in accordance with the prescribed range and frequency of motion, retrieve the current time from the system clock and record the current time in the secondary memory as the start time for disintegration of the dosage unit. After the system has recorded the start time for the disintegration, the system then (iv) receives over a second data communications interface a stream of frames captured over time by the capture device, each frame in the stream of frames comprising image data for an image of the dosage unit in the immersion fluid, (v) store the stream of frames in the frame buffer in the secondary memory, (vi) select a frame from the stream of frames, (vii) retrieve from the frame buffer the image data for the selected frame, (viii) calculate a background differential for the image data for the selected frame, and (ix) compare the background differential to a specified target background differential.

The secondary memory on the computer system includes a collection of records and other data structures, including, for example, a frame buffer and a duration record to record and hold the streams of frames and image data captured over time by the capture device or capture devices, as well as the background differentials and calculated disintegration times.

In general terms, calculating the value of the background differential essentially measures and quantifies, in terms of color, distance and/or temperature, the differences between the disintegrating dosage unit (i.e., the tablet, capsule or granule) in the foreground of each captured image and the surface (or surfaces) that are visible behind dosage unit in each captured image, such as a metal mesh located underneath the dosage unit during the test, or in some cases, the base (or sidewall) of the disintegration tester. The vessel holding the immersion fluid is usually transparent, although transparency of the vessel is not required for embodiments of the present invention to work as intended. There are a number of different ways to calculate the background differential of a frame of image data. In some, but not necessarily all embodiments, the application program repeatedly retrieves the image data for each captured frame from the frame buffer of the secondary memory, and for each frame calculates the background differential for the image data in the frame by: (a) identifying a specified number of centroids in the image data; (b) creating a cluster for each centroid in the image data by determining Euclidian distances between the centroids; (c) assigning each pixel in the image data to one of the clusters by determining Euclidian distances between each pixel and each centroid; (d) counting the number of pixels assigned to each cluster and discarding any cluster that does not contain a specified minimum number of pixels; and (e) setting the background differential equal to the number of clusters remaining after discarding all the clusters having less than the specified minimum number of pixels.

The result is that, as the dosage unit disintegrates over time, the contrast between the colors, distances and/or temperatures of the dosage unit in the foreground of each image and the background in each image will slowly diminish over time until (eventually) only one color (one distance or one temperature) remains in the image. As the number of colors (distances, or temperatures) diminishes for each succeeding frame, so will the number of clusters. As the number of clusters diminishes with successive frames, so will the value of the background differential, until a specified target background differential (such as, for example, a target background differential having the value "1") is reached, signifying that the dosage unit is completely disintegrated. For example, for purposes of this embodiment of the invention, the dosage unit is completely disintegrated when there is only one color (one distance or one temperature) in the image of the current frame. If, for example, the original color of the tablet is white, and the original color of the background is black, then, more likely than not, when the target background differential is reached, the color of every pixel in the frame currently under examination will be some shade of grey. Likewise, if the original color of the tablet is red, and the original color of the background is white, then, more likely than not, when the target background differential is reached, the color of every pixel in the frame currently under examination will be some shade of pink.

Accordingly, the application program includes programming instructions that, for each frame of image data retrieved from the frame buffer, compares the calculated background differential for that frame to the specified target background differential. When the calculated background differential falls to a value that is less than or equal to the specified target background differential (e.g., the value "1"), the programming instructions in the application program will cause the microprocessor to calculate the disintegration time by retrieving from the system clock the current time, subtracting the recorded start time from the current time, and setting the value of the duration record in the secondary memory equal to the calculated disintegration time. On the other hand, if the background differential remains greater than the specified target background differential, the application program will select the next frame from the stream of frames in the frame buffer and repeat for the newly selected frame the steps of calculating the background differential and comparing it to the specified target background differential.

When the calculated background differential is finally less than or equal to the specified target background differential and a value representing the duration of the disintegration has been assigned to the duration record, the microprocessor operating under the control of the application program compares the value to the prescribed time limit. If the duration value is less than or equal to the prescribed time limit, the microprocessor operating under the control of the application program will transmit a signal or message to the output device of the computer system indicating that the test was a success because the dosage unit disintegrated within the prescribed time limit. The application program may further include programming instructions that, when executed by the microprocessor, will cause the microprocessor to transmit a failure indicator to the output device if the dosage unit takes too long to disintegrate, resulting in a duration value in the duration record that is greater than the prescribed time limit.

Suitably, the output device, which may comprise, for example, a display, a printer, a speaker, a light, a network interface, or some other hardware device for communicating information to a human operator, or alternatively, another computer program, such as an email server or webpage server, that can display, print, announce, transmit or otherwise deliver to a human operator a message or signal informing the human operator about the current status, or the success or failure of the dosage unit to completely disintegrate within the prescribed time limit. In addition to providing a message, an audio signal, or turning on or blinking a light, or producing some other signal or alert indicating the success or failure of the test, or as an alternative to it, the application program may also include programming instructions that cause the microprocessor to display the disintegration time (i.e., the duration value of the disintegration) on a display screen or monitor associated with the computer system. For example, the application program may include programming instructions to cause the microprocessor to start and display on the display screen of the computer system a timer that counts and displays the number of seconds elapsed since the recorded start time, and stops counting when the dosage unit is completely disintegrated, as determined by calculating the background differentials for each successively captured frame of image data. The application program may also include programming instructions that cause the microprocessor to activate a speaker on the computer system to produce an audible signal, such as a series of chimes or "beeps" to alert a nearby human operator that the disintegration is complete.

In some situations, and in some embodiments, it may be necessary or desirable to generate and transmit to an output device an error indicator, error message or error signal if the disintegration time for the dosage unit falls outside a prescribed range of allowable completion times. This may be the case, for example, if the dosage unit completely disintegrates faster or slower than it should disintegrate. To provide such an error indicator, error message or error signal, the application program in embodiments of the present invention may also include programming instructions that, when executed by the microprocessor, will cause the microprocessor to periodically perform the following steps while the disintegration is in progress: (a) retrieve the current time from the system clock; (b) calculate an elapsed time for the disintegration by subtracting the start time from the current time; (c) compare the elapsed time to a prescribed range of allowable completion times; and (d) generate and send to the output device an error signal indicating that a duration anomaly has occurred if the elapsed time is outside the prescribed range of allowable completion times.

Because it also may be necessary or desirable to ensure that the temperature of the immersion fluid remains within a prescribed range during the disintegration testing, embodiments of the present invention also may include and utilize a thermal capture device or temperature sensor that periodically detects the current temperature of the immersion fluid. In these cases, the application program will also include programming instructions that, when executed by the microprocessor, will cause the microprocessor to periodically: (i) receive the current temperature of the immersion fluid from the thermal capture device or temperature sensor; (ii) compare the current temperature of the immersion fluid to a specified range of permissible immersion fluid temperatures; and (iii) if the current temperature of the immersion fluid is not within the specified range of permissible immersion fluid temperatures, generate and send to one or more output devices an error message indicating that a temperature anomaly has occurred.

As previously stated, in some embodiments, the apparatus of the present invention includes two or more capture devices, i.e., a first capture device and a second capture device, both of which are attached to the reciprocating arm of the disintegration tester and oriented to capture and transmit two distinct streams of frames, each frame containing image data. The first, second and third capture devices optionally can be removably attached to the reciprocating arm of the disintegration tester. To accommodate the image data generated and transmitted by the second capture device, the apparatus of the of the present invention may also include a second frame buffer in the secondary memory, a second fastener for attaching the second capture device to the reciprocating arm of the disintegration tester or to the first capture device, and a third data communications interface that carries image data from the second capture device to the computer system. In this configuration of the present invention, the application program further includes programming instructions that, when executed by the microprocessor, will cause the microprocessor to: (i) receive over the third data communications interface a second stream of frames captured over time by the second capture device, each frame in the second stream of frames comprising image data for a secondary image of the dosage unit in the immersion fluid, (ii) store the second stream of frames in the second frame buffer of the secondary memory, (iii) select a frame from the second stream of frames, (iv) retrieve from the second frame buffer the image data for the selected frame of the second stream of frames, (v) calculate a second background differential for the image data for the selected frame of the second stream of frames, and (vi) compare the second background differential to a specified second target background differential.

If the second background differential is less than or equal to the specified second target background differential, then the application program will cause the microprocessor to: (vii) store in the secondary memory a second disintegration time that is equal to the current time minus the start time. On the other hand, if the second background differential is greater than the specified second target background differential, then the application program will cause the microprocessor to: (viii) select a new frame from the second stream of frames and repeat steps (iii) through (vii) above until the second background differential is less than or equal to the specified second target background differential. Then the microprocessor, operating under the control of the application program, will compare the second disintegration time stored in the secondary memory to the first disintegration time stored in the secondary memory, and, if the second disintegration time is greater than the first disintegration time, set the duration value in the duration record equal to the second disintegration time.

The application program's performance of these steps effectively causes the microprocessor to always use the longer of the two disintegration times. In other embodiments, the application program may be configured to store, use, output and/or display the shorter, the average or the median value of two or more disintegration times. A similar sequence of steps may be simultaneously carried out when the present invention is implemented with yet another capture device, i.e., a third capture device, a third frame buffer and a fourth data communications interface, thereby permitting the system to calculate and use the longest or "best" disintegration times derived from all three capture devices operating simultaneously to record images of the same disintegrating dosage unit.

In another implementation, embodiments of the present invention provide a method for determining whether a dosage unit of a drug disintegrates within a prescribed time limit in an immersion fluid of a disintegration tester, the method comprising:

(a) attaching a first capture device and a motion sensor to the reciprocating arm of the disintegration tester;

(b) establishing a first data communications channel between the motion sensor and a computer system, the computer system comprising a microprocessor, an output device, a system clock, a primary memory, and a secondary memory, the secondary memory including a first frame buffer and a duration record;

(c) establishing a second data communications channel between the first capture device and the computer system;

(d) receiving on the computer system via the first data communications channel motion data generated by the motion sensor, and determining based on the motion data that the reciprocating arm is moving in accordance with the prescribed range and frequency of motion; and (e) with the microprocessor on the computer system,
(i) retrieving a current time from the system clock and recording the current time in the secondary memory as a start time for disintegration of the dosage unit;
(ii) receiving over the second data communications channel a first stream of frames captured over time by the first capture device, each frame in the first stream of frames comprising image data for an image of the dosage unit in the immersion fluid,
(iii) storing the first stream of frames in the first frame buffer in the secondary memory,
(iv) selecting a frame from the first stream of frames,
(v) retrieving from the first frame buffer the image data for the selected frame,
(vi) calculating a background differential for the image data for the selected frame,
(vii) comparing the background differential to a specified target background differential,
(viii) if the background differential is less than or equal to the specified target background differential, calculating a first disintegration time by subtracting the start time from the current time and set a duration value for the duration record of the secondary memory equal to the first disintegration time,
(ix) if the background differential is greater than the specified target background differential, selecting a new frame from the first stream of frames and repeating steps (e)(vii) through (e)(x) above until the background differential is less than or equal to the specified target background differential, and
(x) transmitting a success indicator to the output device if the duration value is less than or equal to the prescribed time limit.

BRIEF DESCRIPTION OF THE DRAWINGS

The present invention and various aspects, features and advantages thereof are explained in detail below by reference to the exemplary and therefore non-limiting embodiments shown in the figures, which constitute a part of this specification and include depictions of the exemplary embodiments. In these figures:

FIG. 6 shows a table illustrating a prophetic example of the image data that may be generated and stored in one or more frame buffers in accordance with the operation of an embodiment of the present invention.

FIGS. 14A, 14B and 14C show the image data captured in three different frames near the beginning, in the middle and near the end of a disintegration test.

DETAILED DESCRIPTION OF EXEMPLARY EMBODIMENTS

Figure 1:
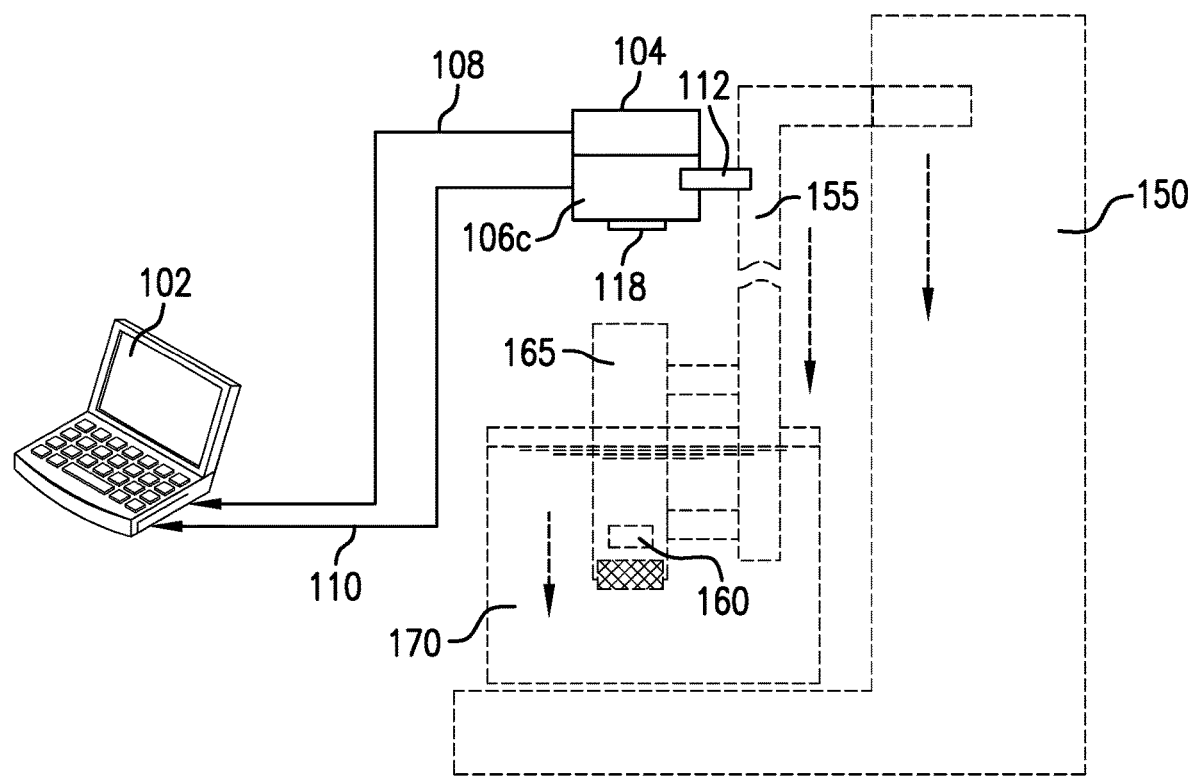
FIGS. 1, 2 and 3 show an exemplary embodiment of the present invention (shown in solid lines) as it would be used with a conventional disintegration tester, which is shown in broken lines.

By way of overview, exemplary embodiments of the present invention provide an apparatus and method for monitoring, recording, displaying and/or transmitting a disintegration time for a dosage unit of a pharmaceutical drug when it is disintegrated in an immersion fluid of a disintegration tester. In some embodiments, the disintegration time (i.e., the time it takes for the dosage unit to disintegrate) recorded by the system may be compared to a time limit prescribed, for example, by a regulatory rule or monograph, in order to determine and indicate to a human operator whether (or not) the disintegration was completed within the prescribed time limit.

Generally, these functions are achieved by utilizing a computer system and one or more capture devices, such as optical, laser and/or thermal capture devices (cameras), to record one or more streams of frames (snapshots) of the dosage unit as the dosage unit disintegrates in the immersion fluid of the disintegration tester. Each frame contains image data representing the image captured in each frame. More specifically, each frame contains image data representative of the individual pixels corresponding to the visible surfaces of the dosage unit in the foreground of each image, as well as the individual pixels corresponding to the visible surfaces of the background in each image (i.e., everything except the dosage unit in the image). For example, if the dosage unit in the image is a bright red pill, and the background in the image comprises a stark white surface of the base wall of the vessel holding the immersion fluid or the base wall of disintegration tester underneath the base wall of the vessel, then, before the disintegration starts to occur, the entire frame will consist largely of image data representing bright red pixels in the center of the image, surrounded by stark white pixels.

As the streams of frames are captured by the capture device(s), the image data in each frame of the stream is stored in a frame buffer of the secondary memory of the computer system. The microprocessor on the computer system, operating under the control of an application program running in the primary memory of the computer system, retrieves from the frame buffer(s) the image data for each successively captured frame and analyzes the image data to calculate and quantify the differences in color, depth and/or temperature between the pixels corresponding to the visible surfaces of the dosage unit in the foreground of each image and the pixels corresponding to the visible surfaces in the background of each image. These color, depth and temperature differences between the surfaces of the dosage unit in each frame and the surfaces of the background in each frame are referred to as "background differential" for each frame.

At the beginning of the disintegration process, the background differential for the image data for each frame captured will be relatively high, owing to the fact that there will likely exist relatively large differences (in terms of color, depth and/or temperature) between the surfaces of the dosage unit in the image foreground and the surfaces of whatever makes up the background of the image, such as a mesh or the base wall of the disintegration tester. As the dosage unit disintegrates in the immersion fluid, the differences in color, depth and/or temperature tend to decrease, thereby decreasing the calculated background differential for each frame. Put another way, the range of different colors, different depths and different temperatures for the many pixels (points) across the entire frame will tend to contract as the dosage unit disintegrates.

Eventually, at the point in time when the dosage unit is completely disintegrated in the immersion fluid, the entire frame (and therefore all the pixels in the frame) will appear to have become substantially the same color, substantially the same depth and/or substantially the same temperature. In other words, for all the pixels in each frame, there will be relatively little, if any, variation in color, depth or temperature. Thus, if the frames captured at (or near) the beginning of the disintegration process depict a bright red pill against a stark white background, then the frames captured at (or near) the end of the disintegration process are very likely to consist almost entirely of pixels that are substantially pinkish in color, albeit with some variation in the pinkish shades from pixel to pixel. Because substantially all the pixels in a frame captured at the end of the disintegration will be pinkish in color, the calculated background differential for that frame will be relatively small, as compared to the background differential calculated for frames captured at the beginning of the disintegration process. When the calculated background differential for one of the capture frames falls below a specified threshold (defined by a specified target background differential) embodiments of the present invention are configured to record the current time, and use the current time to calculate, store and/or transmit to an output device a duration time for the disintegration. An appropriate success or failure message may also be generated, stored and/or transmitted to an output device depending on whether (or not) the recorded duration time falls within a prescribed or expected time range.

For purposes of monitoring and recording disintegration times for dosage units with embodiments of the present invention, disintegration does not require complete dissolution of the dosage unit, or even its active constituent. Complete disintegration is defined as that state in which any residue of the dosage unit, except fragments of insoluble coating or capsule shell, remaining on the screen of the test apparatus is a soft mass having no palpably firm core.

Figure 2:
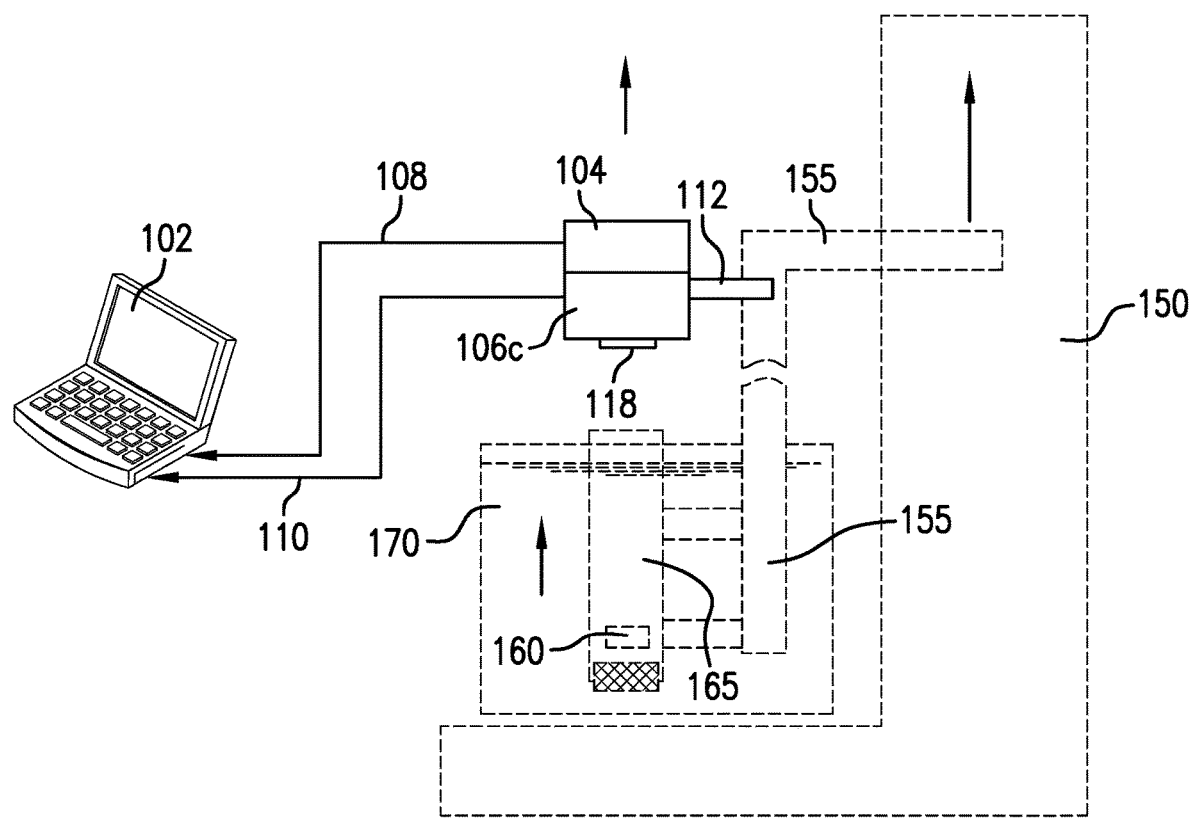
Figure 3:
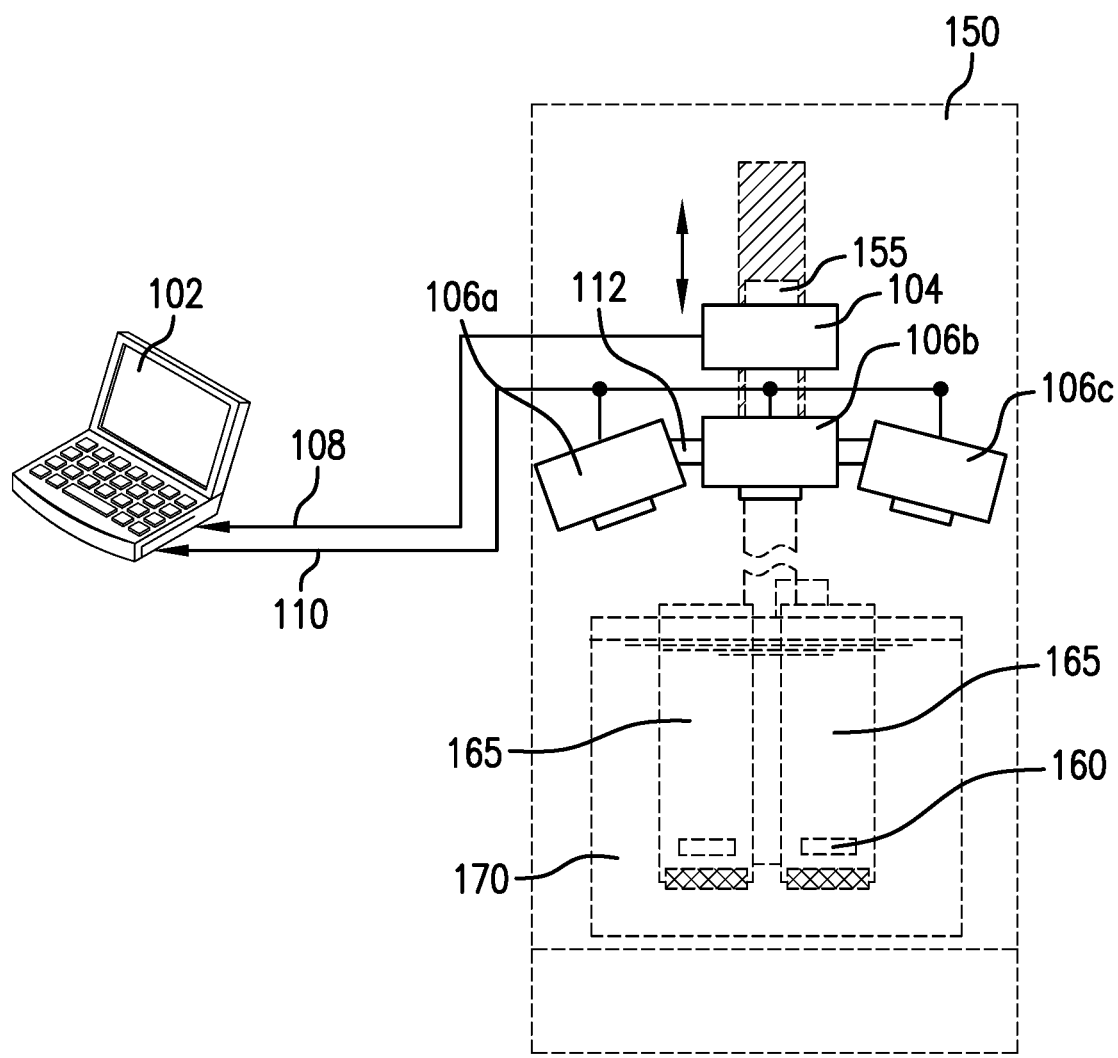

Turning now to the figures, FIGS. 1, 2 and 3 show an exemplary embodiment of the present invention 100, shown in solid lines, as it would be used with a typical example of a conventional disintegration tester 150, shown in broken lines. In FIG. 1, the reciprocating arm 155 of the disintegration tester 150 is in the up (raised) position, while in FIGS. 2 and 3, the reciprocating arm 155 of the disintegration tester 150 is in the down (lowered) position relative to the center position of the up and down range of motion (i.e., the stroke) of the reciprocating arm 155. FIGS. 1 and 2 show the apparatus of the invention with a side view of the disintegration tester 150, and FIG. 3 shows the apparatus of the invention with a front view of the disintegration tester 150. As shown in FIGS. 1 and 2, one embodiment of the present invention comprises a computer system 102, a motion sensor 104 and a single capture device 106c. FIG. 3 shows a different implementation of the present invention, wherein three separate capture devices 106a, 106b and 106c are employed to separately capture and transmit additional images of the dosage unit 160 during the disintegration process.

The motion sensor 104 is communicatively connected to the computer system 102 via a data communications interface 108, which permits the computer system 102 to send commands to and receive motion data from the motion sensor 104. The capture devices 106a, 106b and 106c are communicatively connected to the computer system 102 via a second data communications interface 110, which permits the computer system 102 to send commands to and receive image data from the capture devices 106a, 106b and 106c. Although the data communications interfaces 108 and 110 are shown in FIGS. 1, 2 and 3 as wired connections, it will be recognized and appreciated by those in the art that these data communications interfaces 108 and 110 may instead comprise wireless communications channels without departing from the scope of the disclosed invention. Accordingly, it is understood that the data communication interfaces 108 and 110 may comprise, for example, a universal serial bus (USB) adapter; a wireless radio frequency data communications adapter (e.g., a Bluetooth interface), an Ethernet adapter, a video graphics adapter card and video cable, or any combination of two or more such interfaces, such as would be suitable for communication between the computer system 102 and peripherals designed to detect and transmit motion signals or capture and transmit still and video images.

The capture devices 106a, 106b and 106c typically comprise one or more digital still cameras, digital video cameras, light detection and ranging (LIDAR) cameras, thermal capture devices, or any other device capable of capturing and transmitting image data to the computer system 102. LIDAR is a remote sensing method that uses light in the form of a pulsed laser to measure distances from the LIDAR instrument to an object, such as the surfaces of the dosage unit or surfaces behind the dosage unit. A thermal capture device detects infrared output differentials, so that two objects with the same temperature will appear to be the same "color." Many thermal capture devices use grayscale to represent normal (or room) temperature objects, but highlight warmer surfaces in different colors, such as orange or red. Beneficially, thermal capture devices can "see" through cloudy or opaque fluids, and therefore are capable of producing very accurate data representing "images" of dosage units and backgrounds in immersion fluids, even though the immersion fluids may have become too cloudy or opaque to see with the naked eye due to disintegrating particles and residue in the fluid. The thermal capturing device may also be configured to detect and help monitor the current temperature in the fluid bed, and/or provide a temperature gradient for the fluid bed as the testing proceeds.

For purposes of the present invention, the capture devices 106a, 106b and 106c may be set to capture frames at a variety of different frame rates, such as 15 framers per second (fps), 30 fps, 60 fps or 120 fps, and a variety of different frame sizes, such as 1024×768 pixels, 1280×960 pixels (which is 1 megapixel), 1600×1200 pixels (2 megapixels), 2240×1680 pixels (4 megapixels), or greater, depending on the particular capture device, as well as the processing power of the computer system 102.

The motion sensor 104 and capture devices 106a, 106b and 106c are attached to the reciprocating arm 155 of the disintegration tester 150 with a fastener 112. Non-limiting examples of fasteners that could be used to attach the motion sensor 104 and capture devices 106a, 106b and 106c to the reciprocating arm 155 include, for example, a clasp, snap, pin, clip, clamp, buckle, hook, cable, chain, string, strap, wire, tape, nut, bolt, screw, adhesive, Velcro® strip or Velcro® patch, or zip-tie.

In the example shown in FIGS. 1 and 2, the motion sensor 104 is attached to the capture device 106c, and then the capture device 106c is attached directly to the reciprocating arm 155 with the fastener 112. It should be understood, however, that additional fasteners (not shown in FIG. 1, 2 or 3) could be used to attach the motion sensor 104 directly to the reciprocating arm 155, or to attach the capture devices 106a, 106b and 106c to the motion sensor 104, instead of attaching the capture devices 106a, 106b and 106c directly to the reciprocating arm 155. Preferably, but not necessarily, the motion sensor 104 and capture devices 106a, 106b and 106c are releasably fastened to the reciprocating arm 155 so that the system can more easily be moved around and attached to other disintegration testers as needed. In alternative embodiments, however, the computer system 102, motion sensor 104 and capture devices 106a, 106b and 106c may be permanently attached or built into the disintegration tester 150.

In any event, the motion sensor 104 and the capture device 106 should be attached to each other or to the reciprocating arm 155 of the disintegration tester 150 so that both the motion sensor 104 and the capture device 106 will always move in strict concert with the reciprocating arm 155 whenever the reciprocating arm 155 is in motion, so that the lenses 118 of the capture devices 106a, 106b and 106c are always pointed directly at the dosage units 160 in the bottom of the tube 165, and so that the lenses 118 of the capture devices 106a, 106b and 106c always remain at a constant distance from the dosage unit 160 while the reciprocating arm 155 raises and lowers the dosage unit 160 in the immersion fluid 170.

Figure 4D:
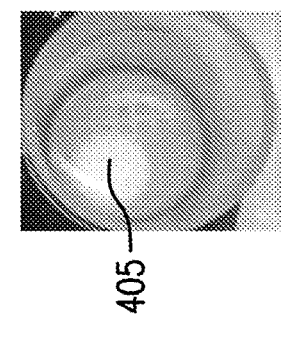
FIGS. 4A through 4H show an example of a sequence of frames captured by a capture device over time, in accordance with embodiments of the present invention, wherein each frame comprises an image of the dosage unit at a different point in time during the disintegration of that dosage unit over time.
Figure 4C:
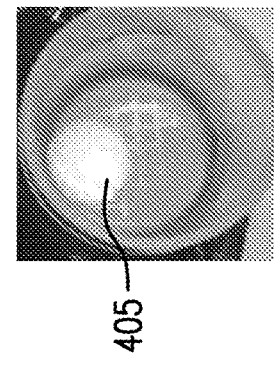
Figure 4B:
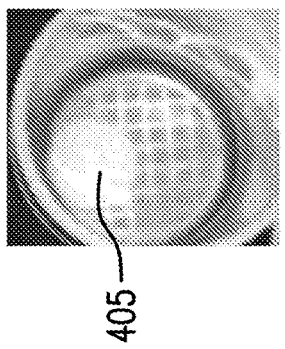
Figure 4A:
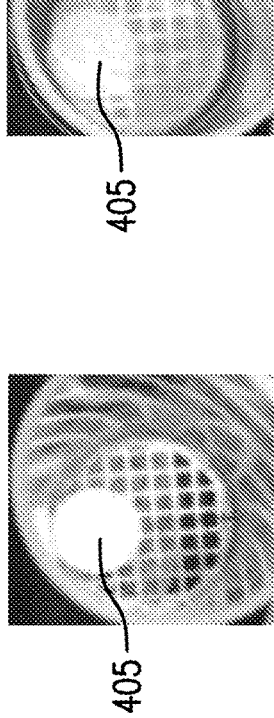
Figure 4H:
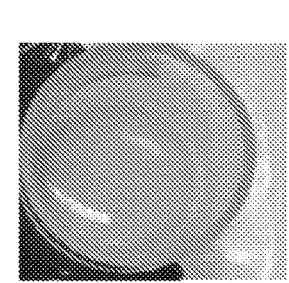
Figure 4G:
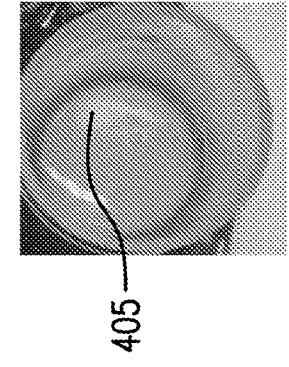
Figure 4F:
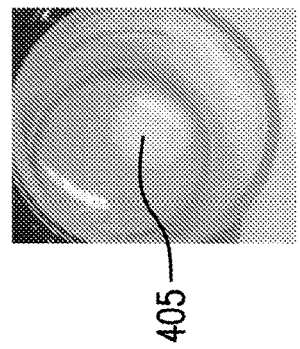
Figure 4E:
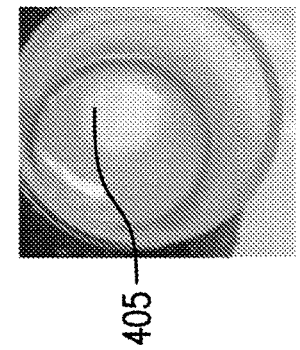

FIGS. 4A through 4H show an example of a sequence of frames captured by an image capture device over time, wherein each frame comprises a single image of the dosage unit in a tube of a basket rack assembly at a different point in time during the disintegration of that dosage unit. The total duration for the disintegration of the tablet in FIGS. 4A-4H is 8 minutes and 24 seconds. A total of eight images were captured at intervals of roughly 64 seconds apart. FIG. 4A shows an image captured early in the process, when the disintegration of the dosage unit 405 is just getting started, while FIG. 4H shows an image captured relatively late in the process. FIGS. 4B through 4G show images captured at various times between the beginning of the process (where there is little or no disintegration) and the end of the process (where there is complete, or almost complete, disintegration).

Figure 5:
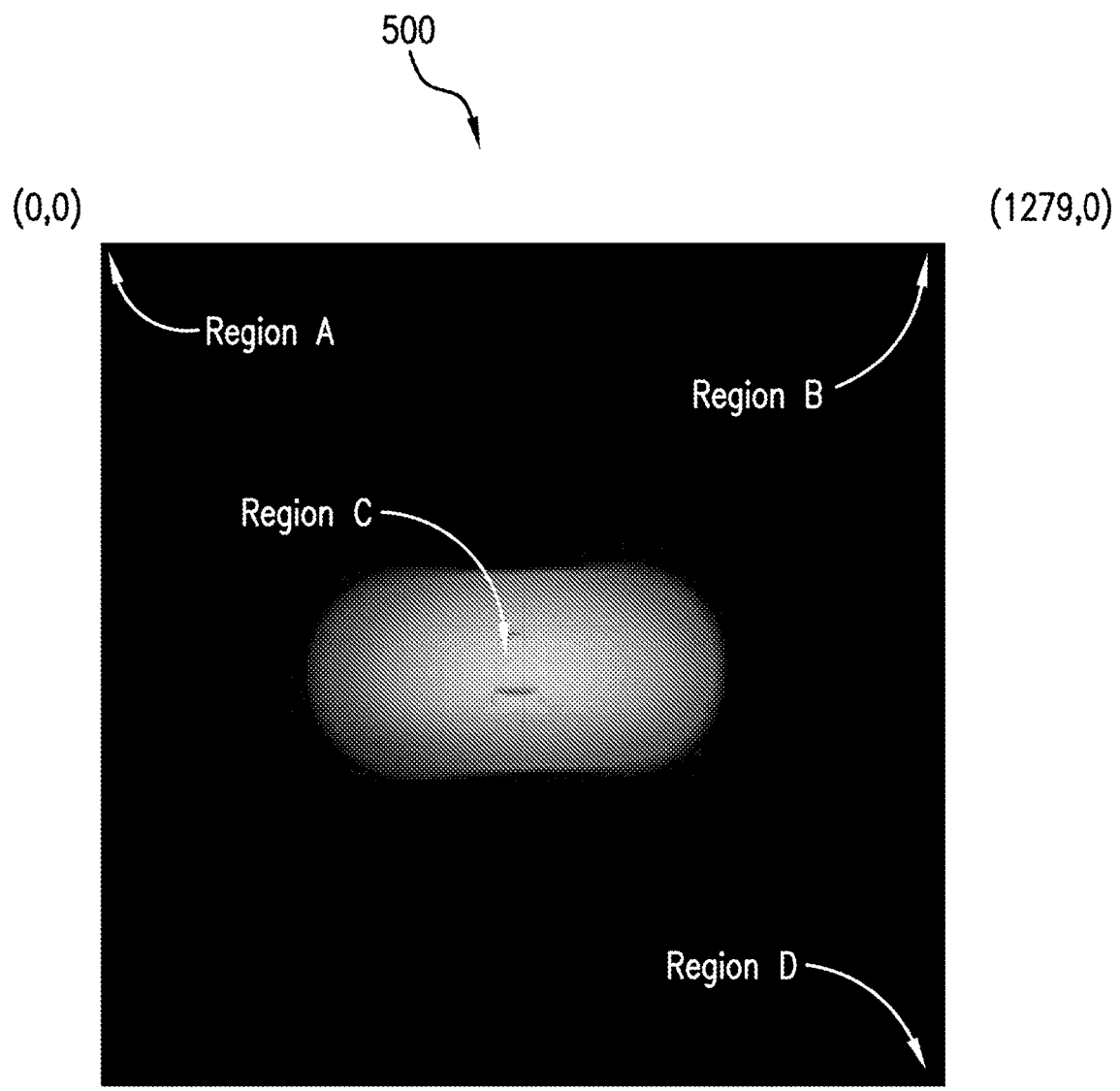
FIG. 5 shows a prophetic example of a single frame captured by a capture device during disintegration of the dosage unit, the single frame comprising a single image of the dosage unit in the immersion fluid.

To illustrate the contents of the image data that may captured in a frame in accordance with the principal of operation of the present invention, FIG. 5 shows a prophetic example of a single frame 500 captured with the capture device 106a, 106b or 106c. As shown in FIG. 5, the image in the frame 500 shows a white tablet on a black background. For discussion purposes, different regions of the frame 500 in FIG. 5 have been labeled regions A, B, C and D, wherein region A is located in the upper left corner of the frame 500, region B is located in the upper right corner of the frame 500, region C lies roughly in the center of the frame 500 (which also happens to be where the dosage unit, i.e., a tablet is located, and region D is located in the lower right corner of the frame 500. In this case, the frame 500 has dimensions of 1280×1280 pixels, and is assumed to have been captured with a capture device, such as a digital camera, three minutes (or 180 seconds) after the starting time of the disintegration process. If the camera takes 30 fps, then the frame 500 shown in FIG. 5 is the $5,400^{th}$ frame captured since the start time (180 seconds×30 fps=5,400 frames). At this point, three minutes into the disintegration process, the tablet in region C is already partially disintegrated, causing it to appear somewhat dark and fuzzy around the edges.

FIG. 6 shows a table illustrating a prophetic example of a collection of image data that may be generated and stored in one or more frame buffers in the secondary memory of the computer system 102, the image data representing color, depth and temperature data corresponding to regions A, B, C and D of the exemplary frame 500 shown in FIG. 5. In the RGB (red, green and blue) color model and the HSV (hue, saturation and lightness) color model, zero values represent the color black (which is technically the absence of all colors). As shown in FIG. 6, the only region in the frame 500 having non-zero RGB and HSV values is region C. This is because region C, which contains the partially disintegrated tablet, is the only region of the frame 500 having pixels that are not black. The table of FIG. 6 also contains exemplary values for the depths of the tablet and the background, as captured by a LIDAR camera. These data for the LIDAR camera (indicating lesser depths around region C of the image), like the data for the digital camera (indicating higher RBG and HSV values in region C of the image), all reflect the fact that the tablet is located in region C of the captured image.

Figure 7:
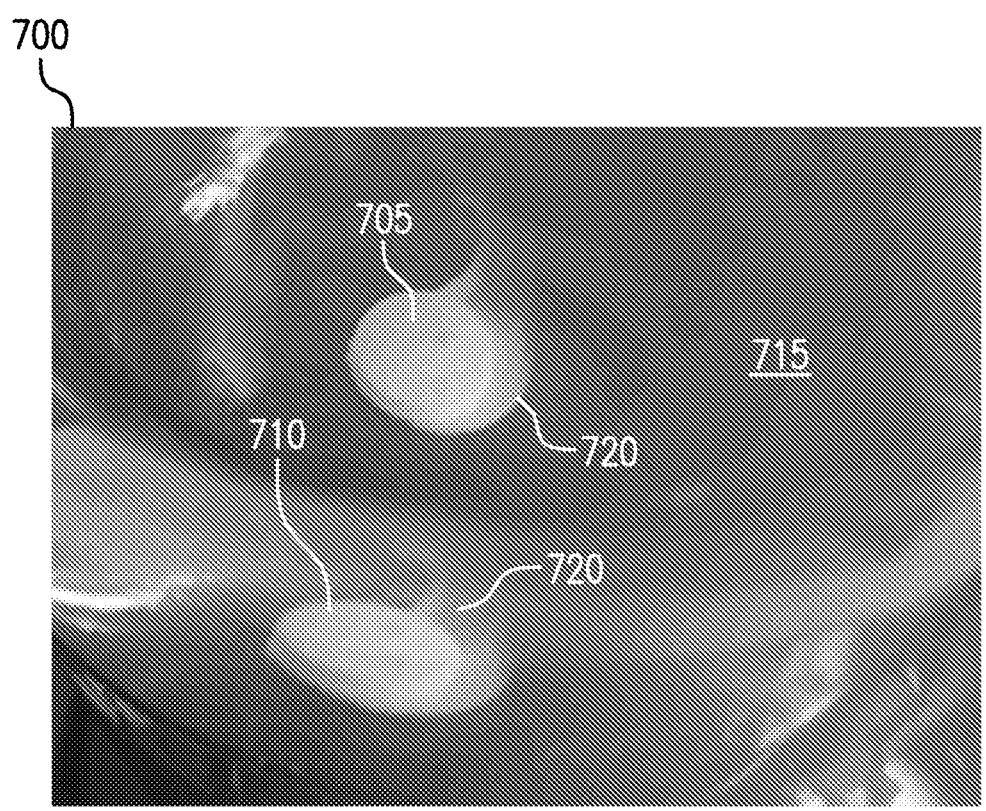
FIG. 7 shows an example of a captured frame of image data for two tablets disintegrating in an immersion fluid.

FIG. 7 shows an example of a captured frame 700 of image data showing two tablets 705 and 710 that are both in the process of disintegrating in an immersion fluid 715. The image data comprises a large number of pixels ranging in color from white, to light grey, to dark grey and to black. The whitest pixels in the image data correspond to the portions of the tablets 705 and 710 that have not disintegrated yet, the blackest (or darkest) pixels in the image correspond to portions of the image corresponding to the color of the black background. As the disintegration of tablets 710 and 715 proceeds, small particles 720 begin to break away from tablets 705 and 710 and get dispersed throughout the immersion fluid 715. As more and more of the tablet particles 720 break off and get carried away from the tablets 705 and 720 by the immersion fluid 715, the immersion fluid 715 slowly becomes more and more opaque, which tends to block more and more of the background from the field of view for the capture device, resulting in successively captured frames having fewer and fewer black pixels in the image, and more and more frames having all grey pixels. Eventually, most of the pixels in a frame will become some shade of grey. In other words, the background differentials in successively-captured frames tend to diminish, eventually falling to a value that is below a predefined background differential threshold. When this happens, embodiments of the present invention may be configured to indicate that the tablets 705 and 710 have completely disintegrated, as described in more detail below with reference to the flow diagrams shown in FIGS. 9 through 11.

Figure 8:
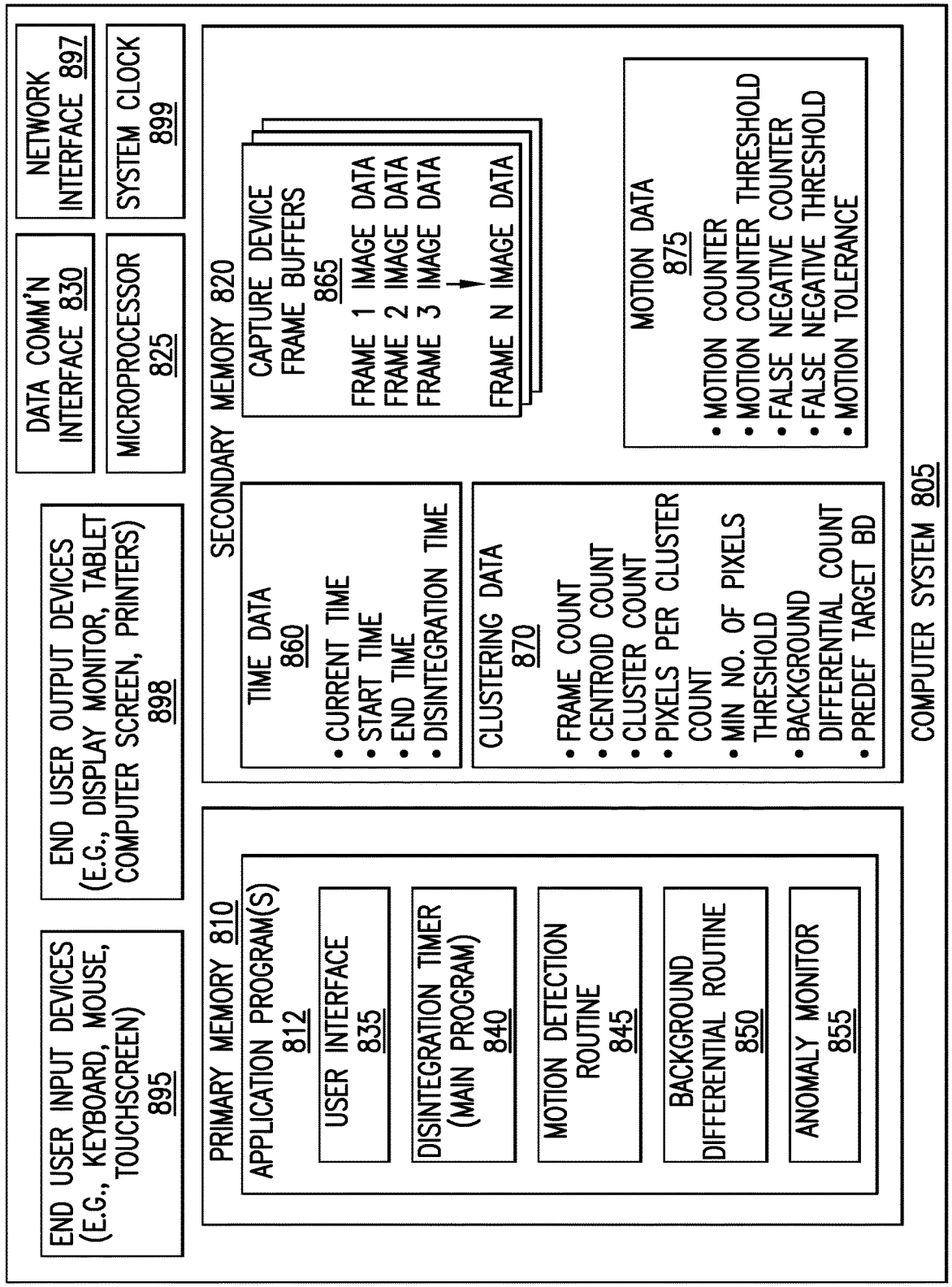
FIG. 8 shows a block diagram illustrating, by way of example, the physical and logical components of a computer system configured to operate according to one embodiment of the present invention.

FIG. 8 shows a block diagram illustrating, by way of example, the physical and logical components of a computer system 805 configured to operate according to one exemplary embodiment of the present invention. The computer system 805 may be implemented on a general purpose or a specialized computer system, including, for example, a personal computer system, a notebook computer, a laptop, tablet or handheld computer system, an Internet-enabled smart phone or personal digital assistant computing device, or any combination of one or more thereof. Typically, the computer system 805 includes a central processing unit (CPU) or microprocessor 825, a primary memory 810 (also called random access memory or RAM), and a non-volatile secondary memory 820 (e.g., a hard drive, a flash drive, or a CD-ROM drive). As shown in FIG. 8, the computer system 805 may also include a network interface 897, such as, for example, a wired Ethernet local area network adaptor, an 802.11 a/g/n WiFi adaptor, a universal serial bus (USB) adaptor, and/or a Bluetooth wireless data communications adaptor, to provide data communication with other computer systems, peripherals such as printers, and/or data communications networks.

Programming instructions or programming code, such as the programming code comprising an application program 812, and program data, such as the time data 860, the clustering data 870, the capture device data frame buffer data 865 and the motion data 875, can be loaded into the primary memory 810 (i.e., loaded into RAM) from the non-volatile secondary memory 820 and provided to the microprocessor 825 for execution. Operating under the control of the application program 812, the microprocessor 825 can generate and store results in the secondary memory 820 for subsequent access, display, output and/or transmission to other computer systems, other computer programs and/or other data communication networks. As shown in FIG. 8, the computer system 805 also includes a system clock 899, which provides the current time to the microprocessor 825, as well as a data communications interface 830, which permits the computer system 805 to receive motion data from the motion sensor 104 and the capture device 106 in real time. Preferably, but not necessarily, the application program 812 also includes programming instructions that, when executed by the microprocessor 825, will cause the microprocessor to send commands to the capture device(s) 106a, 106b and 106c to activate and deactivate the capture devices.

The results of the operations carried out by the microprocessor 825 under the control of the programming instructions in the application program 812 are stored in the secondary memory 820, so that those results can be viewed, navigated and modified, as required, by a human user interacting with the computer system 805 via one or more end user input devices 895 (e.g., a keyboard, mouse, stylus, touchscreen, etc.) and one or more end user output devices 898 (e.g., a display device, a printer, a tablet display screen, or smartphone display screen, etc.) operating under the control of a user interface 835 in the application program 812. The secondary memory 820, and the data it contains, may be integrated into the same physical machine as the microprocessor 825, the primary memory 810, the application program 812 and the software modules 835, 840, 845, 850 and 855, as shown in FIG. 8. However, some or all the data and/or databases shown in the secondary memory 820 may also reside on separate computer systems in a distributed arrangement without departing from the scope of the claimed invention.

The network interface 897 may be employed to establish a connection to remote servers and machines (e.g., mass spectrometer devices) containing or generating additional input data (not shown in FIG. 8) to be processed and a multiplicity of electronic files and documents deemed useful or necessary for carrying out the processes. The network interface 897 may also provide connectivity to remote terminals and/or remote computer systems (not shown) operated by other human users who wish to access and use the computer system 805 of the present invention from a remote location.

The primary memory 810 may comprise without limitation one or more local or remote, fixed or removable, permanent or temporary, magnetic or optical, random access memory (RAM) areas, memory banks or cache memory areas, containing a plurality of program modules for controlling the functions of microprocessor 825 to make the microprocessor 825 perform the methods of measuring and recording disintegration times for dosage units as described herein. Each one of these modules may comprise a computer software program, procedure, or process written as source code in a conventional programming language, which can be presented to the microprocessor 825 for execution by the microprocessor 825. The various implementations of the source code and object and byte codes can be stored on a computer-readable storage medium (such as a DVD, CDROM, floppy disk or memory card) or embodied on a transmission medium or carrier wave before, during or after execution by the microprocessor 825.

The application program 812 comprises a collection of computer software program modules 835, 840, 845, 850 and 855, discussed below, each containing program instructions that, when executed by the microprocessor 825, will cause the microprocessor 825 to perform a variety of specific tasks, as necessary, to receive various types of input data (such as time data 860, capture device data 865 and motion data 875), and to execute the below-described algorithms to generate, store, transmit and display the times associated with the disintegration of dosage units as described herein. These software modules are flexible and may be configured to receive, process and output a large variety of different types of inputs and outputs, including without limitation, alphanumeric text, sounds, images, video, electronic documents, graphs. layouts and schemas. The purpose and function of each one of the computer software modules 835, 840, 845, 850 and 855 in the application program 812 will now be described in more detail below.

The application program 812 includes a user interface 835, a disintegration timer 840, a motion detector routine 845, a background differential routine 850 and an anomaly monitor 855. The user interface 835 comprises program instructions that, when executed by the microprocessor 825, causes the microprocessor 825 to receive and store in the secondary memory 820 certain predefined or prescribed threshold data, such as the specified target background differentials, frequency and range of motion for the reciprocating arm of the disintegration tester, a minimum number of pixels per cluster, a motion tolerance, and false-negative and motion counter thresholds for the motion sensor. The user interface 835 may also include program instructions that, when executed by the microprocessor 825, causes the microprocessor 825 to receive, scan, parse and/or store prescribed time limits for the dosage units under test.

The disintegration timer 840, which is the main program for some embodiments of the present invention, includes program instructions that, when executed by the microprocessor 825, will cause the microprocessor 825 to carry out the steps of the algorithm illustrated by the flow diagram of FIG. 9 (described in more detail below) to determine the disintegration time for a dosage unit under test. The disintegration timer 840 will typically store the calculated disintegration time in the time data 860 section of the secondary memory 820 or some other memory storage area (not shown in FIG. 8) that is connected to or associated with the computer system 805. The motion detector routine 845 carries out the steps of the algorithm illustrated by the flow diagram shown in FIG. 10 (described in more detail below) to determine when the reciprocating arm 155 of the disintegration tester 150 is moving in accordance with a prescribed range and frequency of motion, and record the start time when such prescribed range and frequency of motion is confirmed.

The background differential routine 850 includes program instructions that, when executed by the microprocessor 825, will cause the microprocessor 825 to carry out the steps of the algorithm illustrated by the flow diagram shown in FIG. 11 (described in more detail below) to determine a background differential for each frame retrieved from the capture device frame buffers 865 of the secondary memory. The anomaly monitor 855 includes programming instructions that cause the microprocessor 825 to compare recorded disintegration duration values for the dosage units to prescribed time limits to determine and generate signals, alerts and/or messages to indicate to a human operator whether (or not) the dosage unit under test completely disintegrated within the prescribed time limits. The anomaly monitor 855 may also include programming instructions that cause the microprocessor 825 to compare current immersion fluid temperature readings received from a thermal capture device to a prescribed range of permissible temperatures for the immersion fluid and generate signals, alerts and/or messages to indicate to a human operator whether (or not) the current temperature for the immersion fluid is within the prescribed temperature limits.

Figure 9:
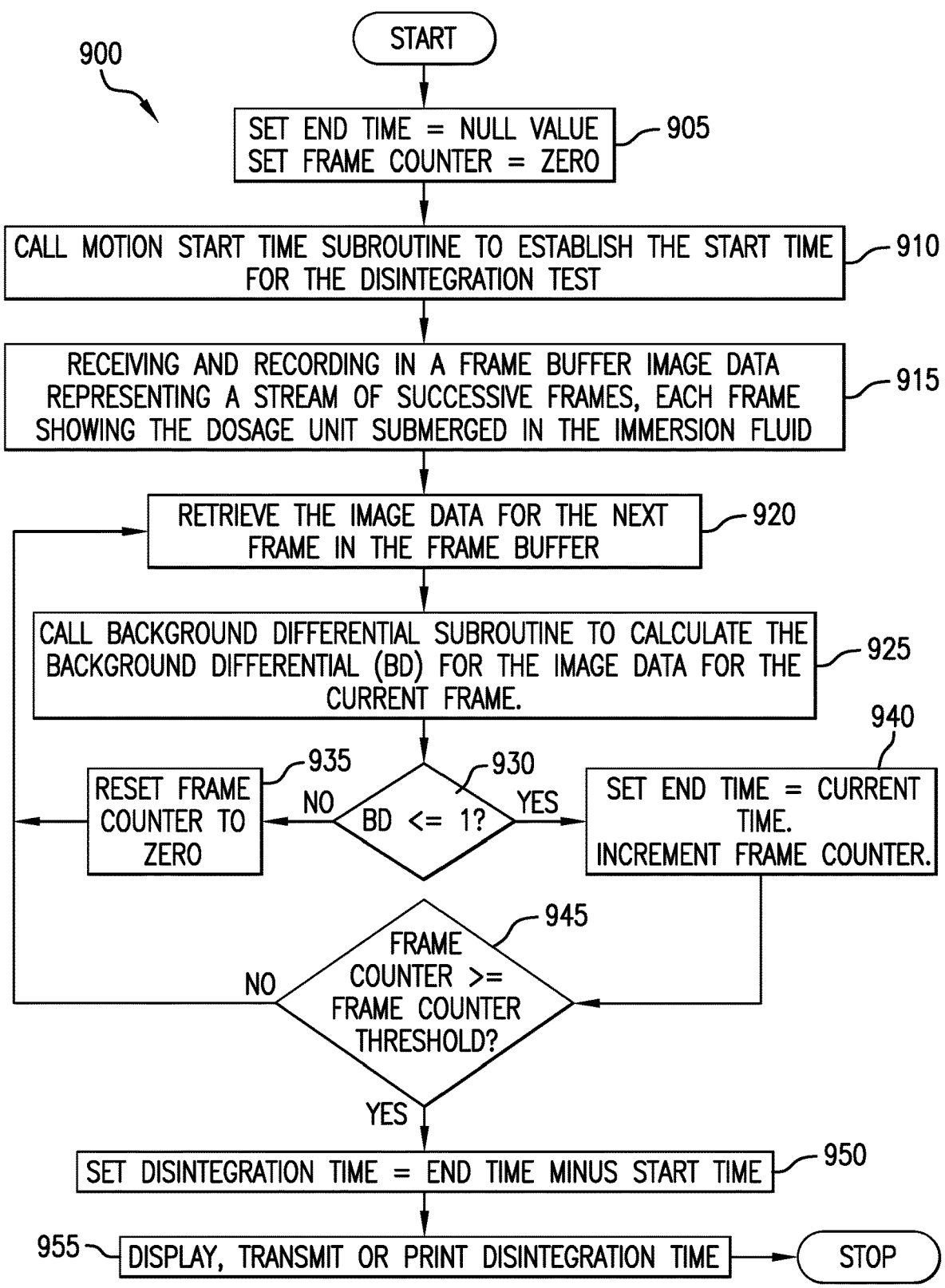
FIG. 9 shows a high-level flow diagram illustrating by way of example the steps performed in an algorithm for determining the disintegration time for one dosage unit of a pharmaceutical drug in accordance with one embodiment of the present invention.

FIG. 9 shows a high-level flow diagram 900 illustrating by way of example the steps of the algorithm performed by the microprocessor 825, operating under the control of the application program 812, to determine the disintegration time for one dosage unit of a pharmaceutical drug in accordance with one embodiment of the present invention. This algorithm serves as the main program in certain, but not necessarily all, implementations and embodiments of the present invention.

As shown in FIG. 9, the main program for determining the disintegration time begins at step 905, wherein the main program sets (or resets) both an end time variable and a frame counter variable in the secondary memory 820 to null and zero, respectively. As will be explained below, the frame counter variable is used to avoid false positives by ensuring that a minimum number of frames (referred to as the frame counter threshold) are determined to have achieved a specified target background differential (which may be referred to as the background differential threshold) before the main program will decide conclusively that the dosage unit has completely disintegrated.

Figure 10:
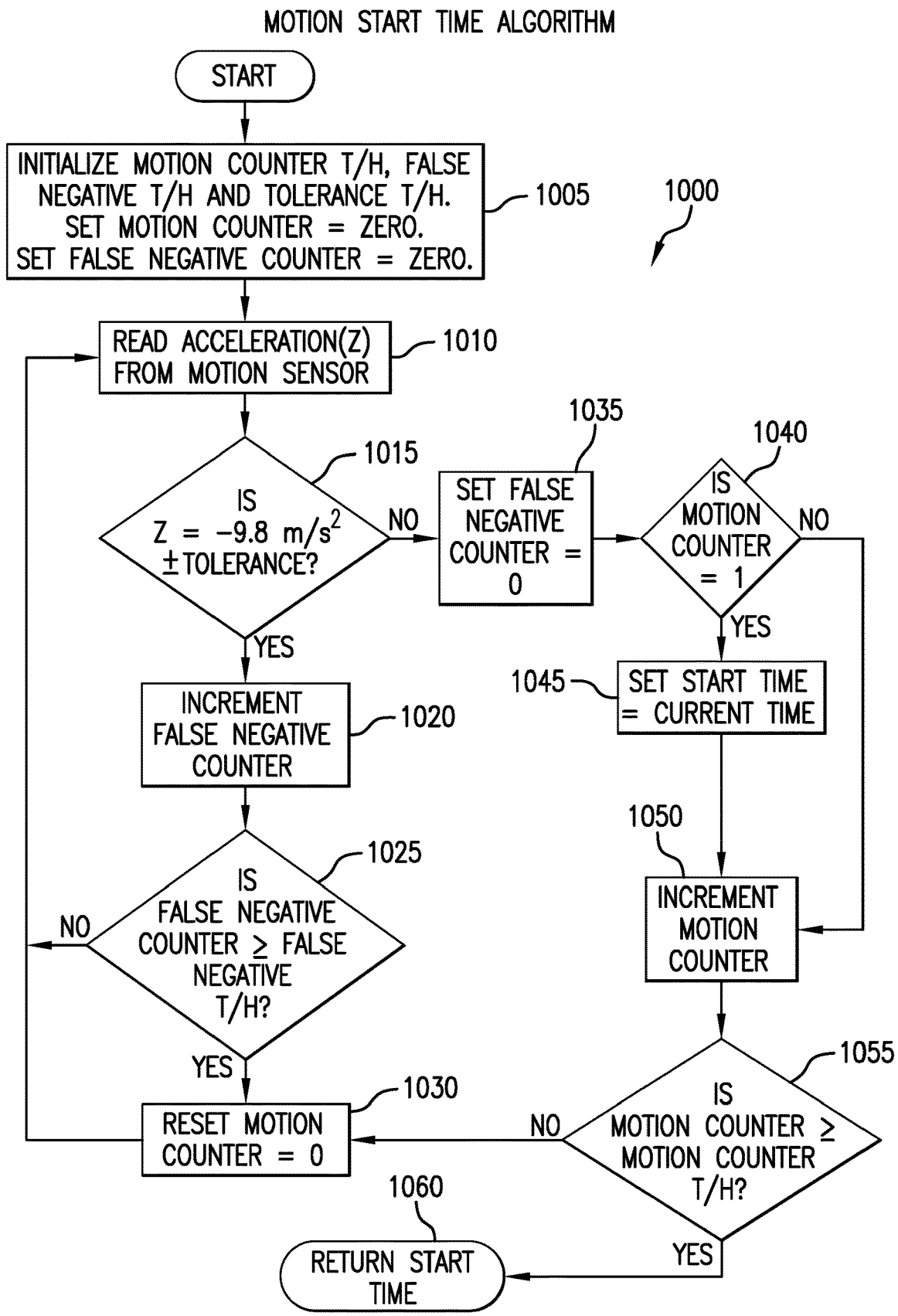
FIG. 10 shows a high-level flow diagram illustrating by way of example the steps performed in an algorithm for determining the start time based on motion data received from a motion sensor in accordance with one embodiment of the present invention.

Next, at step 910, the main program calls the motion start time subroutine to establish and record in the secondary memory the start time for the disintegration test based on the motion sensor sending signals to the microprocessor 825 detecting indicating the reciprocating arm 155 of the disintegration tester 150 has started moving in accordance with a prescribed range and frequency of up and down motion. The details of the algorithm executed by the motion start time subroutine are shown in FIG. 10, which is described in more detail below.

After the motion start time subroutine determines and records a start time for the disintegration, the main program, at step 915 of FIG. 9, starts receiving and recording in a frame buffer image data representing a stream of successive frames captured by the capture device 106, each frame showing the dose unit submerged in the immersion fluid. Preferably, the microprocessor 825 contains multiple cores to enable multithreaded processing, which will permit the microprocessor 825 to efficiently and repetitively receive and record additional frames of image data on a continuous basis for multiple capture devices and/or multiple dosage units in each frame, while at the same time performing the rest of the steps illustrated in the flow diagram of FIG. 9. The more cores a microprocessor has, the more sets of programming instructions the microprocessor can receive and process at the same time, which makes the computer system faster at performing processor-intensive tasks.

Figure 11:
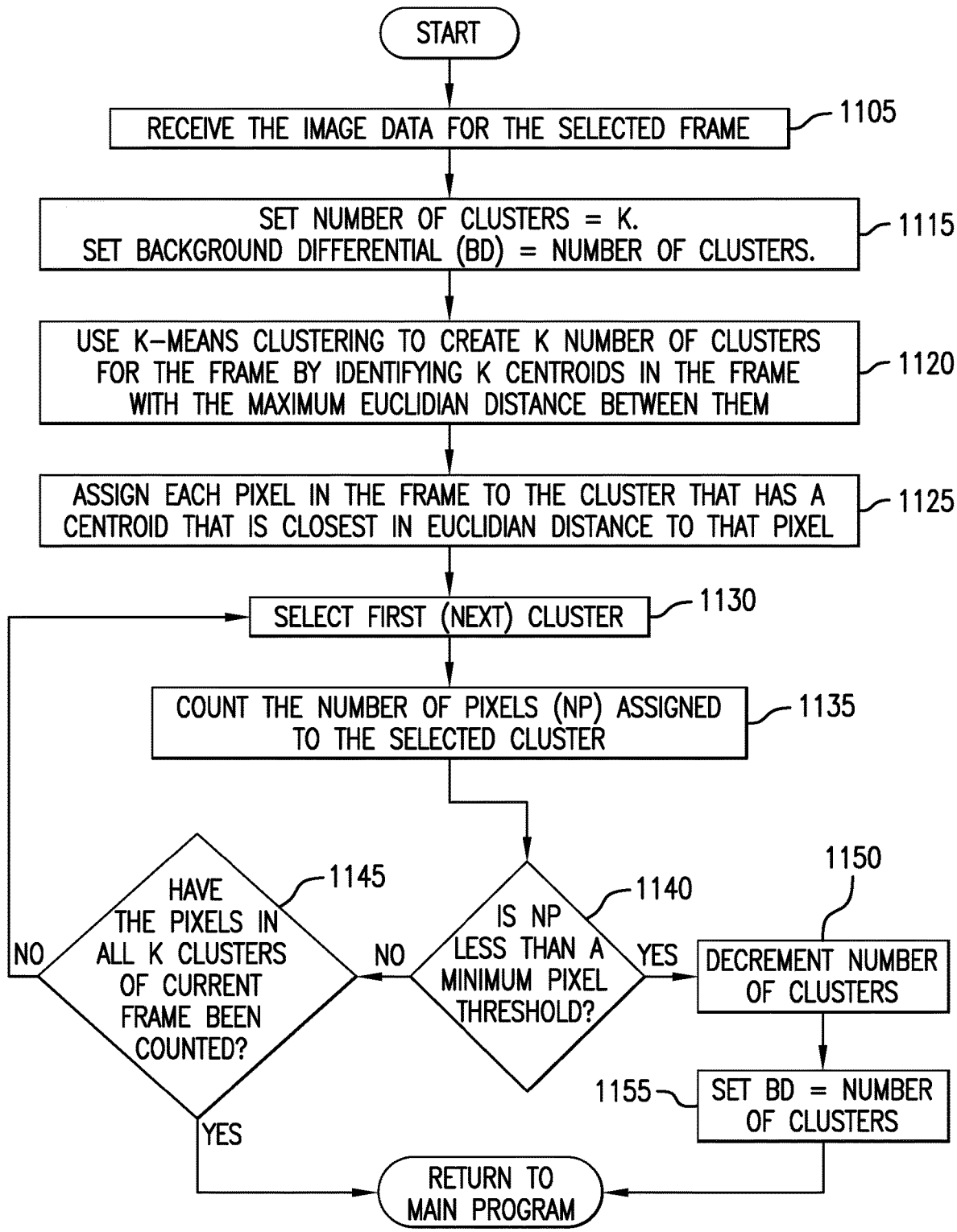
FIG. 11 shows a high-level flow diagram illustrating by way of example the steps performed in an algorithm for calculating the background differential for a frame of image data in accordance with an embodiment of the present invention.

At steps 920 and 925, the main program selects a frame and retrieves from the frame buffer in the secondary memory 820 the image data for the selected frame, and then calls the background differential subroutine illustrated in FIG. 11 to determine the background differential for the selected frame of image data. After the background differential subroutine calculates the background differential for image data of the selected frame, the main program determines, at step 930, whether (or not) the background differential is less than or equal to a specified target background differential (i.e., a background differential threshold), which is 1 in this case. If the answer is no, then the main program resets the frame counter to zero and repeats steps 920, 925 and 930 with the next frame of image data. On the other hand, if it is determined at step 930 that the background differential is less than or equal to 1, then the main program, at step 940, retrieves the current time from the system clock 899, sets the end time equal to the current time, and increments the frame counter to reflect the fact that the background differential threshold has been met by at least one frame in the stream of frames stored in the frame buffer.

At step 945, the main program determines whether (or not) the value of the frame counter is greater than or equal to the value of a specified frame counter threshold. If the answer is "NO," it means the main program has not yet processed enough frames showing that the dosage unit has completely disintegrated to accept that the dosage unit has truly disintegrated. When this is the case, the main program will again return to step 920 and repeat steps 920, 925, 930, 935 and/or 940 with the next frame of image data. Embodiments of the invention may be configured, for example, to keep retrieving and processing successively captured frames of image data until at least five or 10 consecutive frames of image data have met the specified target background differential threshold. This requirement helps the main program avoid false positives that may otherwise arise due to there being stored in the frame buffer abnormal or corrupt frames of image data that do not show the true condition of the dosage unit when the frame was captured.

On the other hand, if it is determined at step 945 that the frame counter variable is greater than or equal to the frame counter threshold, then a sufficient number of consecutive frames have met the target background differential threshold (so there is little or no possibility of a false positive), then the main program will calculate the disintegration time for the dosage unit by subtracting the recorded start time from the recorded end time. See step 950 of FIG. 9. The newly calculated disintegration time may then be displayed, transmitted or printed, as shown in step 955 of FIG. 9, and/or compared to a prescribed time limit, and/or compared to the disintegration times calculated for additional capture devices (not shown in FIG. 9).

FIG. 10 shows a high-level flow diagram 1000 illustrating by way of example the steps performed in the algorithm executed by the motion start time subroutine called at step 910 of FIG. 9 to establish the start time for a disintegration of a dosage unit in a disintegration tester based on motion data received from the motion sensor 104 in accordance with one embodiment of the present invention. First, as shown at step 1005 of FIG. 10, the motion start time subroutine initializes a motion counter threshold, a false-negative threshold, a motion tolerance threshold and false-negative counter by setting or resetting all of these variables to appropriate values. Typically, the counters are all reset to zero, while the thresholds will usually contain non-zero values indicating the number of times a certain event will have to occur before the subroutine will decide conclusively that the occurrence of that event was not just a fluke or a glitch.

Next, at step 1010, the motion start time subroutine will read motion data received from the motion sensor attached to the reciprocating arm 155 of the disintegration tester 150, the motion data indicating the magnitude of vertical acceleration of the motion sensor 104. The motion start time subroutine will then determine, at step 1015, whether the magnitude of the vertical acceleration is equal to the force of gravity ($-9.8$ m/s$^2$), plus or minus the specified motion tolerance threshold. If the answer is "YES," it means the motion sensor and reciprocating arm 155 of the disintegration tester 150 are not moving. Consequently, the motion start time routine increments the false-negative counter (step 1020) and tests to see whether the false-negative counter is greater than or equal to a specified false-negative counter threshold (step 1025). The combined effect of executing steps 1010, 1015 1020 and 1025 is to reduce or eliminate the possibility that the reason the motion sensor 104 and reciprocating arm 155 appear, at least momentarily, to be at a complete standstill is not because the reciprocating arm is not moving, but because the reciprocating arm 155 is moving, and happens to be at the very top or the very bottom of its up and down motion and is therefore in a momentary pause as it reverses direction. If the false-negative counter is not greater than or equal to the false-negative threshold, so that the answer to the question of step 1025 is "NO," control returns to step 1010, in which the system takes another reading of the vertical acceleration of the motion sensor. But if it is determined at step 1025 that the false-negative counter does exceed the false-negative threshold, then the motion counter is reset to zero before control is returned to step 1010.

If it is determined at step 1015 that the magnitude of vertical acceleration of the motion sensor is not equal to the force of gravity, it means the motion sensor 104, and therefore the reciprocating arm 155 of the disintegration tester 150 are in fact moving in a vertical direction, in which case the false-negative counter is reset to zero (step 1035), and the subroutine will then determine whether the motion counter flag is set to "1" (step 1040), which would indicate that the motion sensor has been detected as moving only once. If so, then the motion start time subroutine sets the start time equal to the current time (step 1045), and then increments the motion counter (step 1050). Next, at step 1055, the motion start subroutine checks to determine whether motion counter is greater than or equal to the motion counter threshold. If the answer is "NO," then is reset to zero (step 1030) before control passes back to step 1010 for another reading of the magnitude of the vertical acceleration. But if it is determined at step 1055 that the answer is "YES," then motion start time subroutine returns the value of the start time to the main program and terminates (step 1060).

FIG. 11 shows a high-level flow diagram 1100 illustrating by way of example the steps of the algorithm used by the background differential (BD) subroutine to calculate the background differential for each frame of image data retrieved in accordance with an embodiment of the present invention. The background differential (BD) subroutine calculates the background differential for each frame using an unsupervised machine learning algorithm referred to as "K-means clustering." For purposes of the present invention, all of the pixels in a frame are segregated into a predetermined number of clusters. A cluster refers to a collection of pixels that are grouped together because of their similarity in color. This approach first defines a target number of clusters, "K," to be used for each frame. Each cluster has a centroid. A centroid for a cluster is an imaginary or real color value representing the "center," or average color value, for the cluster. Therefore, the defined value of K also represents the number of centroids for each frame. In other words, the K-means algorithm used in this embodiment of the invention identifies k number of centroids for each frame (which equals the number of clusters for each frame), and then allocates every pixel in the frame to the nearest cluster based on that pixel's similarity, or "closeness," in color to the centroid (the average color) for that cluster.

Returning now to FIG. 11, first, at step 1105, the BD subroutine receives the image data for the selected frame from the frame buffer, and then, at step 1115, initializes the number of clusters by setting the number of clusters to a predetermined value, K. For example, the predetermined value (number of clusters) may be set to a number such as 4 (K="4"). At step 1120, the BD subroutine uses K-means clustering to create K clusters for the selected frame by identifying K centroids in the frame with a maximum Euclidian distance between them. Next, at step 1125, the BD subroutine assigns each pixel in the frame to the cluster that has a centroid that is closest in Euclidian distance to that pixel. Then the BD subroutine selects for processing one of the clusters (see step 1130 of FIG. 11), and then counts the number of pixels assigned to that cluster in the previous step 1125. See step 1135 of FIG. 11.

At step 1140, the BD subroutine determines whether the number of pixels assigned to the currently selected cluster is less than a specified minimum pixel threshold. If the answer is "NO," the BD subroutine checks (at step 1145) to determine whether all the pixels for all the clusters of the current frame have been counted. If not, then control passes back to step 1130, in which the next cluster in the group of K clusters is selected and the pixels in the cluster are counted. If the pixels in all of the clusters of the current frame have been counted (i.e., if the answer to the question at step 1145 is "YES"), then the BD subroutine ends, thereby returning control to the main program to continue performing the steps in the algorithm illustrated by the flow diagram of FIG. 9.

If it is determined at step 1140 that the number of pixels in the selected cluster is less than the specified minimum number of pixels, then the BD subroutine discards (or ignores) that cluster going forward, decrements the cluster count (step 1150), sets the background differential equal to the number of clusters remaining after counting all the pixels assigned to each cluster and discarding any clusters having less than the specified minimum number of pixels (step 1155), and then passes control back to the main program. Notably, when the BD subroutine is done, the number of clusters remaining in the frame is equal to the number of colors remaining in the frame. When the number of colors is "1," the dosage unit disintegration is complete.

Figure 12:
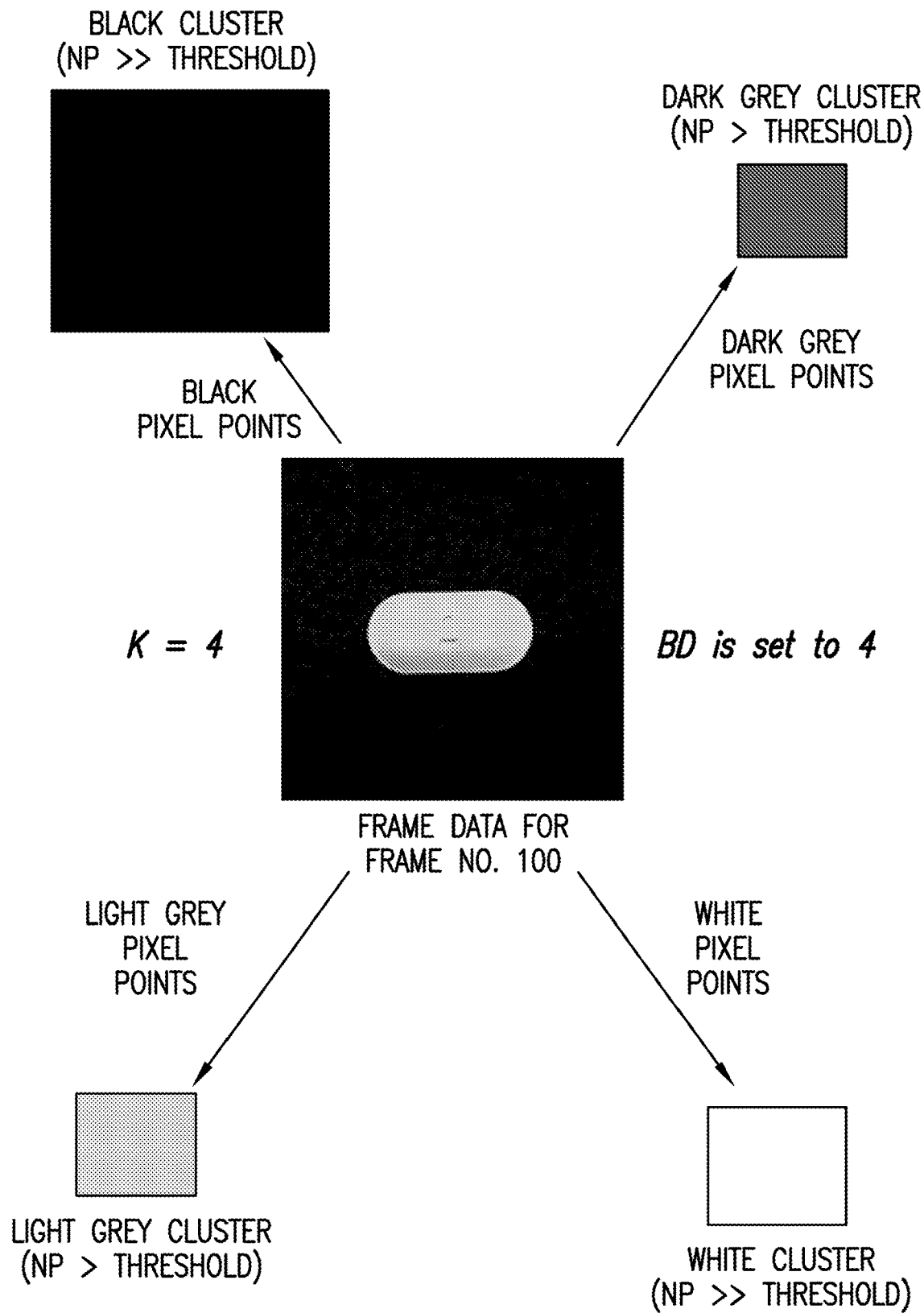
FIG. 12 shows, by way of prophetic example, how the pixels in the image of one frame captured prior to complete disintegration of the dosage unit may be separated and assigned to one of four different clusters based on the colors (or shades) of those pixels according to the algorithm for determining the background differential in one embodiment of the present invention.

FIG. 12 shows, by way of prophetic example, how the pixels in the image of one frame captured prior to complete disintegration of the dosage unit may be separated and assigned to one of four different clusters based on the colors (or shades) of those pixels according to the algorithm illustrated by the flow diagram of FIG. 11, which determines the background differential for each frame of image data retrieved from the frame buffer. FIG. 12 shows the image data for frame No. 100, which is early in the disintegration process. Notably, for frame No. 100, very little disintegration has occurred. Therefore, for frame No. 100, the number of pixels assigned to each one of the four clusters (representing black, white, light grey and dark grey pixels) far exceeds the specified minimum number of pixels, which means none of the 4 clusters will be discarded or ignored. Consequently, the background differential for frame No. 100 will be set to the number of clusters remaining after counting all the clusters having a sufficient number of pixels in them to exceed the minimum number of pixels threshold, which is 4. Because a background differential of "4" exceeds the specified target background differential of "1," the main program (illustrated by the flow diagram of FIG. 9) will conclude that the dosage unit was not disintegrated in frame No. 100, and will therefore continue retrieving and processing the image data for subsequent frames in the frame buffer until a sufficient number of consecutive frames are determined to have calculated background differentials that are less than or equal to the specified target background differential.

Figure 13:
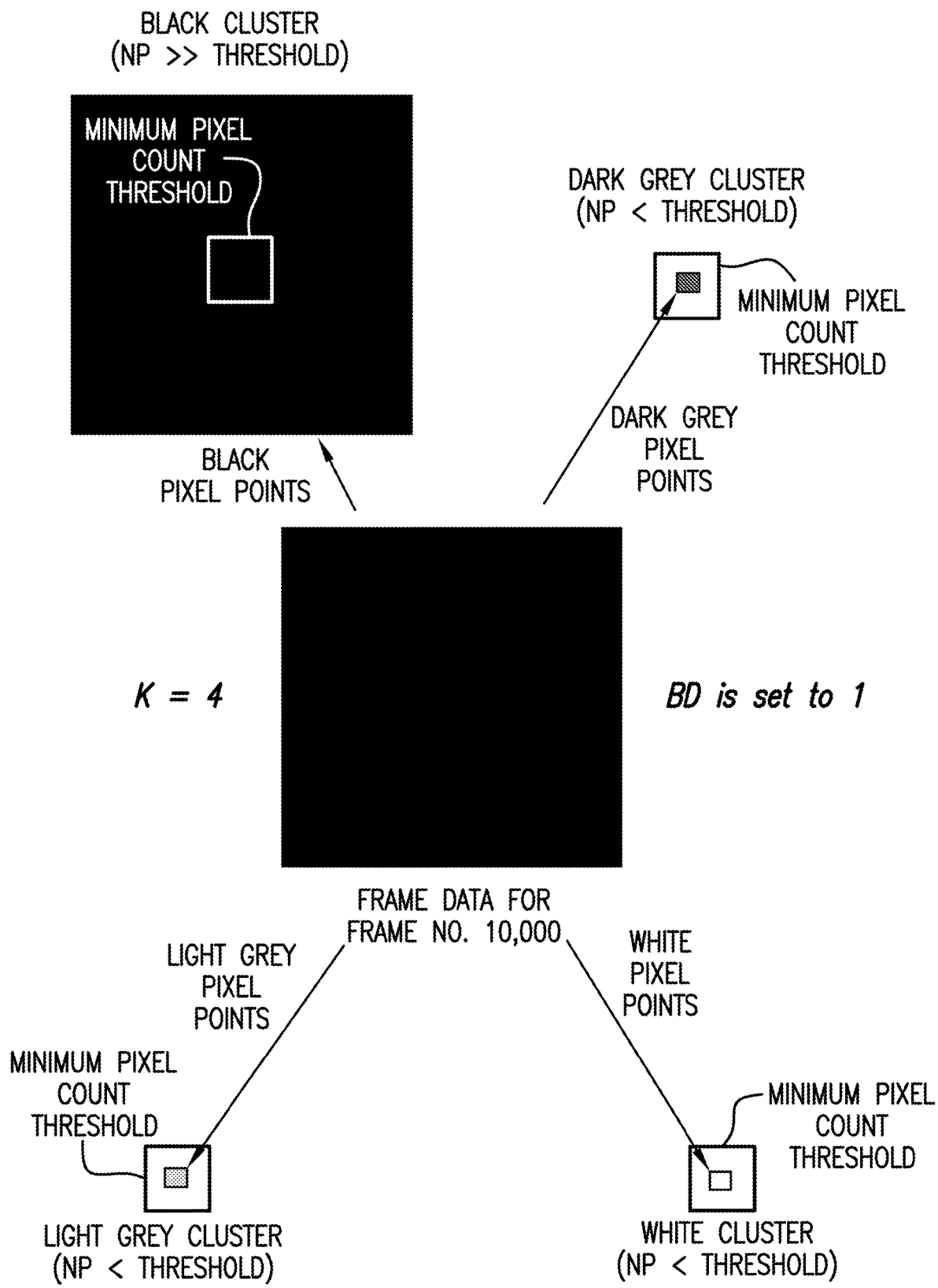
FIG. 13 shows, by way of prophetic example, how the pixels in the image of one frame captured after complete disintegration of the dosage unit may be separated and assigned to one of four different clusters based on the colors (or shades) of those pixels according to the algorithm for determining the background differential in one embodiment of the present invention.

FIG. 13 shows, by way of prophetic example, the image data for frame No. 10,000, which is captured very late in the disintegration process. Notably, for frame No. 10,000, the disintegration is complete and there are very few, if any, white, light grey or dark grey pixels left in the image. Therefore, for frame No. 10,000, the number of pixels that will be assigned to the black cluster will far exceed the specified minimum number of pixels required to retain a cluster, while the number of pixels that will be assigned to the white, light grey and dark grey clusters will be far less than the specified minimum number of pixels, which means the white, light grey and dark grey clusters will be discarded or ignored by the background differential subroutine illustrated by the flow diagram of FIG. 11. Consequently, the background differential for frame No. 10,000 will be set equal to the number of clusters remaining after counting all the clusters with enough pixels to exceed the minimum number of pixels threshold, which is 1. Because a background differential of "1" is less than or equal to the specified target background differential of "1," the main program (illustrated by the flow diagram of FIG. 9) will conclude that the dosage unit was completely disintegrated in frame No. 10,000, and will therefore stop retrieving and processing the image data for subsequent frames in the frame buffer, and record the current time when the processing was stopped.

Figure 14C:
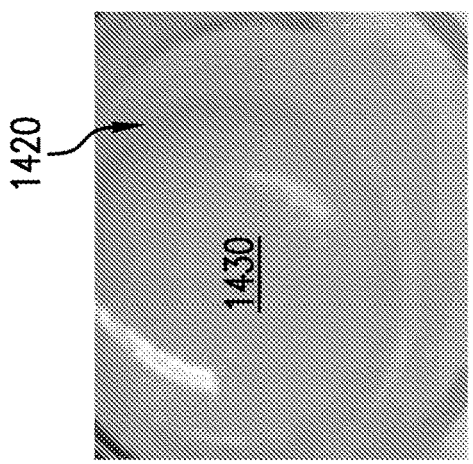
Figure 14A:
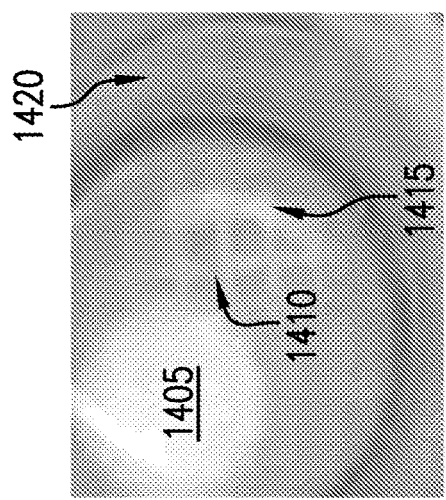
Figure 14A:
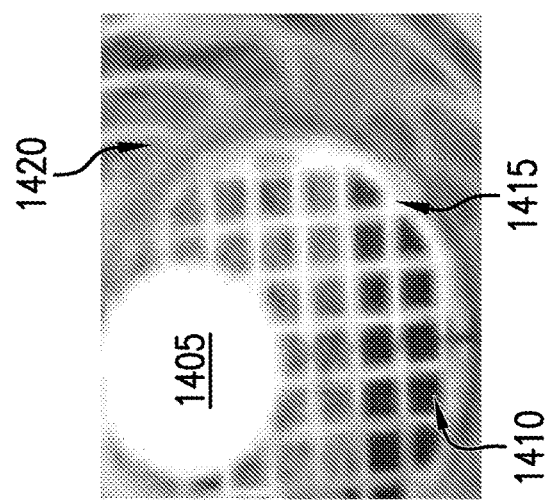

FIGS. 14A, 14B and 14C show the image data captured in three different frames near the beginning, in the middle and near the end of a disintegration test. These images may be captured with the capture device 106a, 106b or 106c. As illustrated by FIGS. 14A, 14B and 14C, the images show a white tablet 1405 on top of a wire mesh 1405 of a tube. Thus, behind the tablet 1405, the image contains and shows portions of the black background 1410, portions of the wire mesh 1415, as well as portions of the inside wall 1420 of the tube containing the tablet 1405 and wire mesh 1415. In FIG. 14A, which was captured earlier in the disintegration process, it can be seen that many black pixels, many white pixels and many pixels have various shades of grey in the frame, ranging from white to black. However, as the tablet disintegrates, the number of black pixels, as well as the number of grey pixels in each succeeding from decreases over time, as shown in the frame shown in FIG. 14B, which was captured later in time than the image shown in FIG. 14A, but earlier in time than the image shown in FIG. 14C, which was captured near the end of the disintegration process. The image shown in FIG. 14B has many more grey pixels, and many less black or white pixels than the image shown in FIG. 14A, while the image shown in FIG. 14C has many more grey pixels than the image shown in FIG. 14B. Eventually, when the tablet 1405 is completely disintegrated, the frame should contain substantially all grey pixels (or at least a very narrow range of substantially grey pixels as compared to the range of black, white and grey pixels depicted in FIGS. 14A and 14B. When the system uses the background differential algorithm described herein to detect that all or most of the pixels in a frame fall within a very narrow range of colors, it means that that frame corresponds to the end of the disintegration process. The breadth of the color range considered to correspond to the end of the disintegration is configurable by setting the maximum of clusters (the value "K") to a specified values, as explained in more detail above with reference to the algorithm illustrated by the flow diagram shown in FIG. 11.

While the invention has been described in detail with reference to specific examples, it will be apparent to one skilled in the art that various modifications can be made within the scope of this invention. Thus, the scope of the invention should not be limited by the examples described herein, but by the claims presented below.

What is claimed is:

1. An apparatus for determining whether a dosage unit of a drug disintegrates in an immersion fluid of a disintegration tester within a prescribed time limit, the disintegration tester including a reciprocating arm that repetitively moves the dosage unit up and down in the immersion fluid in accordance with a prescribed range and frequency of motion, the apparatus comprising:

(a) a computer system comprising a microprocessor, an output device, a system clock, a primary memory, and a secondary memory, the secondary memory including a first frame buffer and a duration record;

(b) a motion sensor;

(c) a first capture device;

(d) a fastener for attaching the first capture device to the reciprocating arm of the disintegration tester;

(e) a first data communications interface that carries motion data from the motion sensor to the computer system;

(f) a second data communications interface that carries image data from the first capture device to the computer system;

(g) an application program, in the primary memory of the computer system, comprising program instructions that, when executed by the microprocessor, will cause the microprocessor to (i) receive motion data from the motion sensor over the first data communications interface, (ii) determine, based on the motion data, that the reciprocating arm is moving in accordance with the prescribed range and frequency of motion, (iii) after determining that the reciprocating arm is moving in accordance with the prescribed range and frequency of motion, retrieve a current time from the system clock and record the current time in the secondary memory as a start time for disintegration of the dosage unit, (iv) receive over the second data communications interface a first stream of frames captured over time by the first capture device, each frame in the first stream of frames comprising image data for an image of the dosage unit in the immersion fluid, (v) store the first stream of frames in the first frame buffer in the secondary memory, (vi) select a frame from the first stream of frames, (vii) retrieve from the first frame buffer the image data for the selected frame, (viii) calculate a background differential for the image data for the selected frame, (ix) compare the background differential to a specified target background differential, (x) if the background differential is less than or equal to the specified target background differential, calculate a first disintegration time by subtracting the start time from the current time and set a duration value for the duration record of the secondary memory equal to the first disintegration time, (xi) if the background differential is greater than the specified target background differential, select a new frame from the first stream of frames and repeat steps (g)(vii) through (g)(x) of this claim until the background differential is less than or equal to the specified target background differential, and (xii) transmit a success indicator to the output device if the duration value is less than or equal to the prescribed time limit.

2. The apparatus of claim 1, wherein the application program further comprises programming instructions that, when executed by the microprocessor, will cause the microprocessor to transmit a failure indicator to the output device if the duration value is greater than the prescribed time limit.

3. The apparatus of claim 1, wherein the application program further comprises programming instructions that, when executed by the microprocessor, will cause the microprocessor to calculate the background differential for the image data for the selected frame by:
   (a) identifying a specified number of centroids in the image data;
   (b) creating a cluster for each centroid in the image data by determining Euclidian distances between the centroids;
   (c) assigning each pixel in the image data to one of said clusters by determining Euclidian distances between said each pixel and said each centroid;
   (d) for each cluster, counting the number of pixels assigned to said cluster and discarding said cluster if the number of pixels in said cluster does not exceed a specified minimum number of pixels; and
   (e) setting the background differential equal to a number of clusters remaining after counting all the pixels assigned to each cluster and discarding any clusters having less than the specified minimum number of pixels.

4. The apparatus of claim 1, wherein the output device comprises a display, or a printer, or an audio speaker, or a light, or an electronic mail server, or a web server, or a data communications network, or a combination of one or more thereof.

5. The apparatus of claim 1, wherein the application program further comprises programming instructions that, when executed by the microprocessor, will cause the microprocessor to:
   (a) retrieve the current time from the system clock;
   (b) calculate an elapsed time for the disintegration by subtracting the start time from the current time;
   (c) compare the elapsed time to a prescribed range of allowable completion times; and
   (d) if the elapsed time is outside the prescribed range of allowable completion times, generate and send to the output device an error signal indicating that a duration anomaly has occurred.

6. The apparatus of claim 1, further comprising:
   (a) a temperature sensor that repetitively detects a current temperature of the immersion fluid;
   (b) wherein the application program further comprises programming instructions that, when executed by the microprocessor, will cause the microprocessor to
      (i) receive the current temperature of the immersion fluid from the temperature sensor,
      (ii) compare the current temperature of the immersion fluid to a specified range of permissible immersion fluid temperatures, and
      (iii) if the current temperature of the immersion fluid is not within said specified range of permissible immersion fluid temperatures, generate and send to the output device an error message indicating that a temperature anomaly has occurred.

7. The apparatus of claim 1, further comprising:
(a) a second capture device;
(b) a second frame buffer in the secondary memory;
(c) a second fastener for attaching the second capture device to the reciprocating arm of the disintegration tester or to the first capture device; and
(d) a third data communications interface that carries image data from the second capture device to the computer system;
(e) wherein the application program further comprises programming instructions that, when executed by the microprocessor, will cause the microprocessor to
   (i) receive over the third data communications interface a second stream of frames captured over time by the second capture device, each frame in the second stream of frames comprising image data for a secondary image of the dosage unit in the immersion fluid,
   (ii) store the second stream of frames in the second frame buffer of the secondary memory,
   (iii) select a frame from the second stream of frames,
   (iv) retrieve from the second frame buffer the image data for the selected frame of the second stream of frames,
   (v) calculate a second background differential for the image data for the selected frame of the second stream of frames,
   (vi) compare the second background differential to a specified second target background differential,
   (vii) if the second background differential is less than or equal to the specified second target background differential, store in the secondary memory a second disintegration time that is equal to the current time minus the start time, and
   (viii) if the second background differential is greater than the specified second target background differential, select a new frame from the second stream of frames and repeat steps (e)(iii) through (e)(vii) of this claim until the second background differential is less than or equal to the specified second target background differential.

8. The apparatus of claim 7, wherein the application program further comprises programming instructions that, when executed by the microprocessor, will cause the microprocessor to:
   (a) compare the second disintegration time stored in the secondary memory to the first disintegration time stored in the secondary memory; and
   (b) if the second disintegration time is greater than the first disintegration time, set the duration value in the duration record equal to the second disintegration time.

9. The apparatus of claim 7, further comprising:
   (a) a third capture device;
   (b) a third frame buffer in the secondary memory; and
   (c) a third fastener for attaching the third capture device to the first capture device, or to the second capture device, or to the reciprocating arm of the disintegration tester;
   (d) a fourth data communications interface that carries image data from the third capture device to the computer system;
   (e) wherein the application program further comprises programming instructions that, when executed by the microprocessor, will cause the microprocessor to
      (i) receive over the fourth data communications interface a third stream of frames captured over time by the third capture device, each frame in the third stream of frames comprising image data for a tertiary image of the dosage unit in the immersion fluid, (ii) store the third stream of frames in the third frame buffer of the secondary memory, (iii) select a frame from the third stream of frames, (iv) retrieve from the third frame buffer the image data for the selected frame of the third stream of frames, (v) calculate a third background differential for the image data for the selected frame of the third stream of frames, (vi) compare the third background differential to a specified third target background differential, (vii) if the third background differential is less than or equal to the specified third target background differential, store in the secondary memory a third disintegration time that is equal to the current time minus the start time, and (viii) if the third background differential is greater than the specified third target background differential, select a new frame from the third stream of frames and repeat steps (e)(iii) through (e)(vii) of this claim until the third background differential is less than or equal to the specified third target background differential.

10. The apparatus of claim 9, wherein the application program further comprises programming instructions that, when executed by the microprocessor, will cause the microprocessor to:

(a) compare the third disintegration time to the first disintegration time and the second disintegration time stored in the secondary memory, and (b) if the third disintegration time is greater than both the first disintegration time and the second disintegration time stored in the secondary memory, set the duration value of the duration record equal to the third disintegration time.

11. A method for determining whether a dosage unit of a drug disintegrates within a prescribed time limit in an immersion fluid of a disintegration tester, the disintegration tester including a reciprocating arm that repetitively moves the dosage unit up and down in the immersion fluid in accordance with a prescribed range and frequency of motion, the method comprising:

(a) attaching a first capture device and a motion sensor to the reciprocating arm of the disintegration tester;

(b) establishing a first data communications channel between the motion sensor and a computer system, the computer system comprising a microprocessor, an output device, a system clock, a primary memory, and a secondary memory, the secondary memory including a first frame buffer and a duration record;

(c) establishing a second data communications channel between the first capture device and the computer system;

(d) receiving on the computer system via the first data communications channel motion data generated by the motion sensor, and determining with the microprocessor, based on the motion data, that the reciprocating arm is moving in accordance with the prescribed range and frequency of motion; and (e) with the microprocessor on the computer system, (i) retrieving a current time from the system clock and recording the current time in the secondary memory as a start time for disintegration of the dosage unit;

(ii) receiving over the second data communications channel a first stream of frames captured over time by the first capture device, each frame in the first stream of frames comprising image data for an image of the dosage unit in the immersion fluid, (iii) storing the first stream of frames in the first frame buffer in the secondary memory, (iv) selecting a frame from the first stream of frames, (v) retrieving from the first frame buffer the image data for the selected frame, (vi) calculating a background differential for the image data for the selected frame, (vii) comparing the background differential to a specified target background differential, (viii) if the background differential is less than or equal to the specified target background differential, calculating a first disintegration time by subtracting the start time from the current time and set a duration value for the duration record of the secondary memory equal to the first disintegration time, (ix) if the background differential is greater than the specified target background differential, selecting a new frame from the first stream of frames and repeating steps (e)(vii) through (e)(x) of this claim until the background differential is less than or equal to the specified target background differential, and (x) transmitting a success indicator to the output device if the duration value is less than or equal to the prescribed time limit.

12. The method of claim 11, further comprising transmitting a failure indicator to the output device if the duration value is greater than the prescribed time limit.

13. The method of claim 11, wherein the step of determining the background differential for the image data for the selected frame comprises:

(a) executing programming instructions on the microprocessor to cause the microprocessor to identify a specified number of centroids in the image data;

(b) executing programming instructions on the microprocessor to cause the microprocessor to create a cluster for each centroid in the image data by determining Euclidian distances between the centroids;

(c) executing programming instructions on the microprocessor to cause the microprocessor to assign each pixel in the image data to one of said clusters by determining Euclidian distances between said each pixel and said each centroid;

(d) executing programming instructions on the microprocessor to cause the microprocessor to, for each cluster, count the number of pixels assigned to said cluster and discard said cluster if the number of pixels in said cluster does not exceed a specified minimum number of pixels; and (e) executing programming instructions on the microprocessor to cause the microprocessor to set the background differential equal to a number of clusters remaining after counting the pixels assigned to each cluster and discarding any clusters having less than the specified minimum number of pixels.

14. The method of claim 11, wherein the output device comprises a display, or a printer, or an audio speaker, or a light, or an electronic mail server, or a web server, or a data communications network, or a combination of one or more thereof.

15. The method of claim 11, further comprising executing programming instructions with the microprocessor, which cause the microprocessor to:

(a) retrieve the current time from the system clock;

(b) calculate an elapsed time for the disintegration by subtracting the start time from the current time;

(c) compare the elapsed time to a prescribed range of allowable completion times; and (d) if the elapsed time is outside the prescribed range of allowable completion times, generate and send to the output device an error signal indicating that a duration anomaly has occurred.

16. The method of claim 11, further comprising:
(a) attaching a temperature sensor to the first capture device or to the reciprocating arm of the disintegration tester; and
(b) executing programming instructions on the microprocessor that cause the microprocessor to
  (i) receive a current temperature of the immersion fluid from the temperature sensor,
  (ii) compare the current temperature of the immersion fluid to a specified range of permissible immersion fluid temperatures, and
  (iii) if the current temperature of the immersion fluid is not within said specified range of permissible immersion fluid temperatures, generate and send to the output device an error message indicating that a temperature anomaly has occurred.

17. The method of claim 11, further comprising:
(a) attaching a second capture device to the first capture device or to the reciprocating arm of the disintegration tester;
(b) establishing a third data communications channel to carry image data from the second capture device to the computer system; and
(c) executing programming instructions on the microprocessor of the computer system to cause the microprocessor to
  (i) receive over the third data communications channel a second stream of frames captured over time by the second capture device, each frame in the second stream of frames comprising image data for a secondary image of the dosage unit in the immersion fluid,
  (ii) store the second stream of frames in a second frame buffer in the secondary memory,
  (iii) select a frame from the second stream of frames,
  (iv) retrieve from the second frame buffer the image data for the selected frame of the second stream of frames,
  (v) calculate a second background differential for the image data for the selected frame of the second stream of frames,
  (vi) compare the second background differential to a specified second target background differential,
  (vii) if the second background differential is less than or equal to the specified second target background differential, store in the secondary memory a second disintegration time that is equal to the current time minus the start time, and
  (viii) if the second background differential is greater than the specified second target background differential, select a new frame from the second stream of frames and repeat steps (c)(iii) through (c)(vii) of this claim until the second background differential is less than or equal to the specified second target background differential.

18. The method of claim 17, further comprising executing programming instructions on the microprocessor to cause the microprocessor to:
(a) compare the second disintegration time stored in the secondary memory to the first disintegration time stored in the secondary memory; and
(b) if the second disintegration time is greater than the first disintegration time, set the duration value in the duration record equal to the second disintegration time.

19. The method of claim 17, further comprising:
(a) attaching a third capture device to the first capture device, or to the second capture device, or to the reciprocating arm of the disintegration tester;
(b) establishing a fourth data communications channel to carry image data from the third capture device to the computer system; and
(c) executing programming instructions on the microprocessor of the computer system to cause the microprocessor to
  (i) receive over the fourth data communications channel a third stream of frames captured over time by the third capture device, each frame in the third stream of frames comprising image data for a tertiary image of the dosage unit in the immersion fluid,
  (ii) store the third stream of frames in a third frame buffer in the secondary memory,
  (iii) select a frame from the third stream of frames,
  (iv) retrieve from the third frame buffer the image data for the selected frame of the second stream of frames,
  (v) calculate a third background differential for the image data for the selected frame of the third stream of frames,
  (vi) compare the third background differential to a specified third target background differential,
  (vii) if the third background differential is less than or equal to the specified third target background differential, store in the secondary memory a third disintegration time that is equal to the current time minus the start time, and
  (viii) if the third background differential is greater than the specified third target background differential, select a new frame from the third stream of frames and repeat steps (c)(iii) through (c)(vii) of this claim until the second background differential is less than or equal to the specified target background differential.

20. The method of claim 19, further comprising executing on the microprocessor programming instructions to cause the microprocessor to:
(a) compare the third disintegration time to the first disintegration time and the second disintegration time stored in the secondary memory, and
(b) if the third disintegration time is greater than both the first disintegration time and the second disintegration time stored in the secondary memory, set the duration value of the duration record equal to the third disintegration time.

* * * * *